(12) United States Patent
Weissmann et al.

(10) Patent No.: US 11,873,531 B2
(45) Date of Patent: Jan. 16, 2024

(54) EDITING PROFILING OF PDE8A PRE-MRNA: USE AS SPECIFIC BIOMARKER OF ADARS ACTIVITIES IN HUMAN TISSUES TO DIAGNOSE AND TO PREDICT AND ASSESS THERAPEUTIC EFFICACY AND/OR EFFICIENCY OR POTENTIAL DRUG SIDE EFFECTS

(71) Applicant: ALCEDIAG, Peynier (FR)

(72) Inventors: Dinah Weissmann, Paris (FR); Jean-Francois Pujol, Paris (FR); Laurent Cavarec, Vincennes (FR); Laurent Vincent, La Ville du Bois (FR)

(73) Assignee: ALCEDIAG, Peynier (FR)

( * ) Notice: Subject to any disclaimer, the term of this patent is extended or adjusted under 35 U.S.C. 154(b) by 239 days.

(21) Appl. No.: 17/090,583

(22) Filed: Nov. 5, 2020

(65) Prior Publication Data
US 2022/0073984 A1     Mar. 10, 2022

Related U.S. Application Data

(60) Continuation of application No. 16/442,825, filed on Jun. 17, 2019, now Pat. No. 10,851,420, which is a division of application No. 15/479,648, filed on Apr. 5, 2017, now Pat. No. 10,323,283, which is a continuation of application No. 13/959,928, filed on Aug. 6, 2013, now abandoned, which is a continuation of application No. 13/805,902, filed as application No. PCT/EP2011/060644 on Jun. 24, 2011, now abandoned.

(60) Provisional application No. 61/344,298, filed on Jun. 24, 2010.

(51) Int. Cl.
*C12P 19/34*     (2006.01)
*C12Q 1/6883*     (2018.01)

(52) U.S. Cl.
CPC ..... *C12Q 1/6883* (2013.01); *C12Q 2600/136* (2013.01); *C12Q 2600/142* (2013.01); *C12Q 2600/158* (2013.01)

(58) Field of Classification Search
CPC .................................... C12Q 1/6883
See application file for complete search history.

(56) References Cited

FOREIGN PATENT DOCUMENTS

WO    WO-2008152146 A1 * 12/2008 ........... C12Q 1/6883

* cited by examiner

*Primary Examiner* — Kenneth R Horlick
(74) *Attorney, Agent, or Firm* — Arrigo, Lee, Guttman & Mouta-Bellum, LLP; Carla Mouta-Bellum

(57) ABSTRACT

The present invention relates to the use of the editing profile of PDE8A pre-mRNA as a specific bio marker of ADARs activities in evolved primate, particularly in Human tissues. The present invention also relates to an in vitro method for predicting in Human an alteration of the mechanism of the ADARs catalysed pre-mRNA editing of target genes, by analysing the PDE8A pre-mRNA editing profile in a peripheral tissue sample containing cells expressing said PDE8A pre-mRNA, such as blood sample. The present invention is also directed to an in vitro method for the screening of potential therapeutic compound and to predict and assess therapeutic efficacy and/or efficiency or to diagnose potential severe brain or peripheral drug side effects implementing said PDE8A pre-mRNA editing profile as specific biomarker. The present invention is further directed to a method for determining the PDE8A pre-mRNA editing profile in Human, particularly by capillary electrophoresis single-strand conformation polymorphism (CE-SSCP) method after amplification by a nested PCR. Finally the invention relates to particular nucleic acid primers implemented in said nested PCR and kit comprising such sets of primers and human cells capable of expressing PDE8A and ADARs.

15 Claims, 15 Drawing Sheets

Figure 3A:
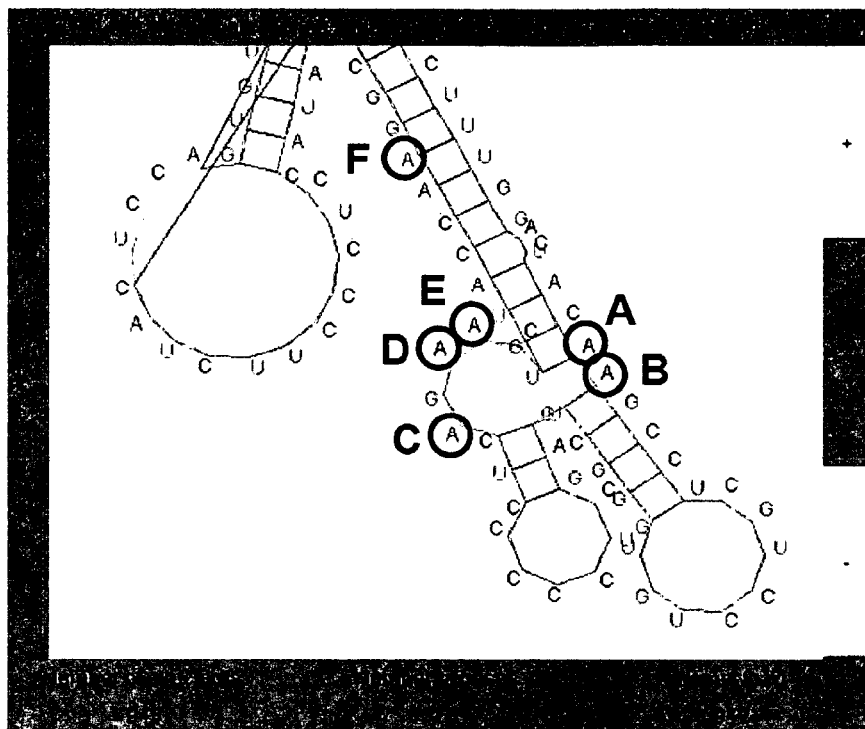

Specification includes a Sequence Listing.

SEQ ID NO. 1: Partial sequence of Intron 9 of the *PDE8A* gene(432bp)

```
Ggttcttagtatattcacagttttgcaaatgtcacaattaatttcccatattccccttgata
Gtgagctttagaagtaacccttagacctgtctgctgaagccttccttctaaggtagacatgc
                                        H
aagttgtggacatggaggacaacccacttatttctgcctagggaaccctgtttagtccttgg
            AB                            C DE          F
tggctttggactacaagcctcgtcctgtgggctgagctcccctcagaactgtaccaaggcc
catacctcccttctactccagtgtgacctaaggactcagctgggctttctggctgtttttg
  G
atatagccctttttggtgcccattgttttcagaattatatcagtaagcatcagtaatcatc
ctttgattctatcggagtattctggtttcttttgatctgctttcccagaggagtctgaa
```

FIGURE 1

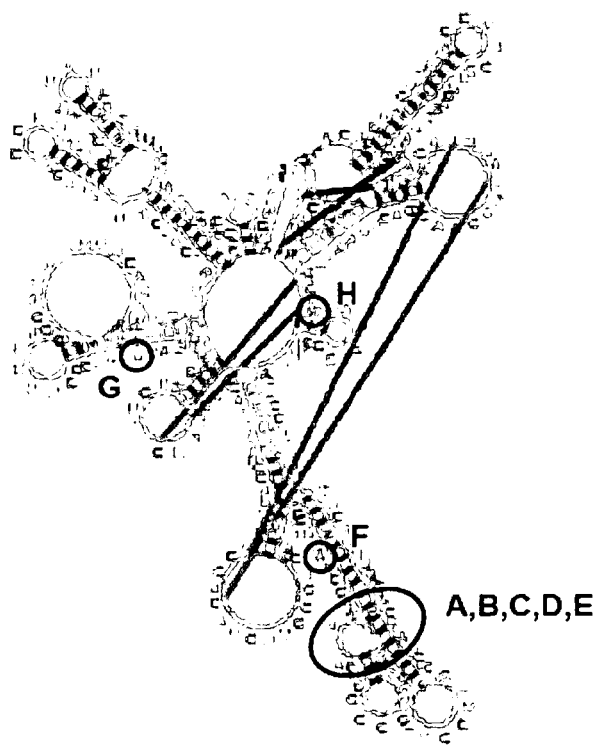

Free-energy : -99.1 kcal/mol

FIGURE 2

Query: SEQ ID NO.1
Sbjct: SEQ ID NO.2

```
Query    1       ggttcttagtatattcacagttttgcaaatgtcacaattaATTTCCCATATTCCCCTTGA
                 ||||||||||||||||||||||||||||||||||||||||||||||||||||||||||||
Sbjct    606890  GGTTCTTAGTATATTCACAGTTTTGCAAATGTCACAATTAATTTCCCATATTCCCCTTGA Query    61      TAGTGAGCTTTAGAAGTAACCCTTAGACCTGTCTGCTGAAGCCTTCCTTCTAAGGTAGAC
                 ||||||||||||||||||||||||||||||||||||||||||||||||||||||||||||
Sbjct    606950  TAGTGAGCTTTAGAAGTAACCCTTAGACCTGTCTGCTGAAGCCTTCCTTCTAAGGTAGAC
                                                                             H
Query    121     ATGCAAGTTGTGGACATGGAGGACAACCCACTTATTTCTGCCTAGGGAACCCTGTTTAGT
                 ||||||||||||||||||||||||||||||||||||||||||||||||||||||||||||
Sbjct    607010  ATGCAAGTTGTGGACATGGAGGACAACCCACTTATTTCTGCCTAGGGAACCCTGTTTAGT
                                           AB                            C DE
Query    181     CCTTGGTGGCTTTGGACTACAAGCCTCGTCCTGTGGGCTGAGCTCCCCCTCAGAACTGTA
                 ||||||||| |||||||||||||||| |||||||||||||||||||||||||||||||||
Sbjct    607070  CCTTGGTGGTTTTGGACTACAAGCCTTGTCCTGTGGGCTGAGCTCCCCCTCAGAACTGTA
                          F
Query    241     CCAAGGCCCATACCTCCCTTCTACTCCAGTGTGACCTAAGGACTCAGCTGGGCTTTCTGG
                 ||||||||||||||||||||||||||||||||||||||||||||||||||||||||||||
Sbjct    607130  CCAAGGCCCATACCTCCCTTCTACTCCAGTGTGACCTAAGGACTCAGCTGGGCTTTCTGG
                            G
Query    301     CTGTTTTTGATATAGCCCTTTTTGGTGCCCATTGTTTTCAGAATTATATCAGTAAGCA
                 ||||||||||||||||||||||||||||||||||||||||||||||||||||||||||||
Sbjct    607190  CTGTTTTTGATATAGCCCTTTTTGGTGCCCATTGTTTTCAGAATTATATCAGTAAGCA Query    361     TCAGTAATCATCCTTTGATTCTATCGGAGTATTCTGGTTTCTTTTGATCTGCTTTCCCA
                 |||||||||||||||||||||||| | |||||||||||||||||||||||||||||||||
Sbjct    607250  TCAGTAATCATCCTTTGATTCTGTTGGAGTATTCTGGTTTCTTTTGATCTGCTTTCCCA Query    421     GAGGAGTCTGAA    432
                 ||||||||||||
Sbjct    607310  GAGGAGTCTGAA    607321
```

FIGURE 4

Query : SEQ ID NO.1
Sbjct : SEQ ID NO.3

```
Query    1       ggttcttagtatatattcacagttttgcaaatgtcacaattaATTTCCCATATTCCCCTTGA
                 ||||  ||||||||||||| ||||||||||||||||||||    ||||  |||||||||||
Sbjct    565681  GGTTTTTAGTATATTCATGGTTTTGCAAATGTCACAATT----TCCCGTATTCCCCTTGA Query    61      TAGTGAGCTTTAGAAGTAACCCTTAGACCTGTCTGCTGAAGCCTTCCTTCTAAGGTAGAC
                 |||||||||| |||||||||||||||||||||||| |||||||||||||||||||||| |
Sbjct    565625  TAGTGAGCTTCAGAAGTAACCCTTAGACCTGTCTCCTGAAGCCTTCCTTCTAAGGTAGGC
                                                                             H
Query    121     ATGCAAGTTGTGGACATGGAGGACAACCCACTTATTTCTGCCTAGGGAACCCTGTTTAGT
                 |||||||||||||| ||||||| |||||||||||||||||||||||||||||||||||||
Sbjct    565565  ATGCAAGTTGTGGATATGGAGAACAACCCACTTATTTCTGCCTAGGGAACCCTGTTTAGT
                                AB                                C DE
Query    181     CCTTGGTGGCTTTGGACTACAAGCCTCGTCCTGTGGGCTGAGCTCCCCCTCAGAACTGTA
                 |||| | || ||||||||| |||||||||||| ||||||||||||| |||||||||||||
Sbjct    565505  CCTTAGCGGTTTTGGACTGCCAGCCTCGTCCTCTGGGCTGAGCTCCGCCTCAGAACTGTA
                     F
Query    241     CCAAGGCCCATACCTCCCTTCTACTCCAGTGTGACCTAAGGACTCAGCTGGGCTTTCTGG
                 | |||||||||||||||||||||| ||||||||| ||||||||| |||||||||||||||
Sbjct    565445  CTAAGGCCCATACCTCCCTTCTTCTCCAGTGTGAGCTAAGGACTTAGCTGGGCTTTCTGG
                  G
Query    301     CTGTTTTTTGATATAGCCCTT-TTTTGGTGCCCATTGTTTTCAGAATTATATCAGTAAGC
                 ||||||||||||||||||||| |||||||||||||||||||||||||||      || ||||
Sbjct    565385  CTGTTTTTTGATATAGCCCTTTTTTTGGTGCCCATTGTTTTCAGAATT-----AGGAAGC Query    360     ATCAGTAATCATCCTTTGATTCTATCGGAGTATTCTGGTTTCTTTTTGATCTGCTTTCCC
                 ||||||||||||| |||||||||||||||||||| |||||||||||||||||||||||||
Sbjct    565330  ATCAGTAATCATCTTTTGATTCTATCGGAGTATCCTGGTTTCTTTTTGATCTGCTTTCCT Query    420     AGAGGAGTCTGAA      432
                 |||||||||||||
Sbjct    565270  AGAGGAGTCTGAA      565258
```

FIGURE 5

SEQ ID NO. 4

```
ataaagaaagtatactatttggtggttcttagtatattcacagttttgca
aatgtcacaattaatttcccatattcccttgatagtgagctttagaagt
aaccttagacctgtctgctgaagccttccttctaaggtagacatgcaag
                                      H
ttgtggacatggaggacaacccacttatttctgcctagggaaccctgttt
I                        J    K  AB
AgtccttggtggctttggActAcaagcctcgtcctgtgggctgagctccc
       C DE       L  F                        M
cctcagaactgtAccaaggcccatacctccttctactccAgtgtgacct
            N                              G
aaggactcAgctgggctttctggctgttttttgatatagcccttttttgg
tgccattgttttcagaattatatcagtaagcatcagtaatcatcctttg
attctatcggagtattctggtttcttttgatctgctttcccagaggagt
ctgaagatgagctcttatcattggtatttggatgcaggttgccatgtacc
aaacaagaatatttcagaattgacctggagtagggctctggatagcaaac
ctcagctaagccaacaaggctgccatggtgcttaacacccagcctggtc
aactctaggtcctgagggactctggaaggctaagaaaggttatggaatac
cctaggggttcagtgtcctgttgtgggttttagggatttccatagtttaa
gggccttggtgatttcttggaggaattcataacattttaggacggtgac
aaaacccagctccatcctggctttccctaccacccaagataaagggagt
```

FIGURE 6

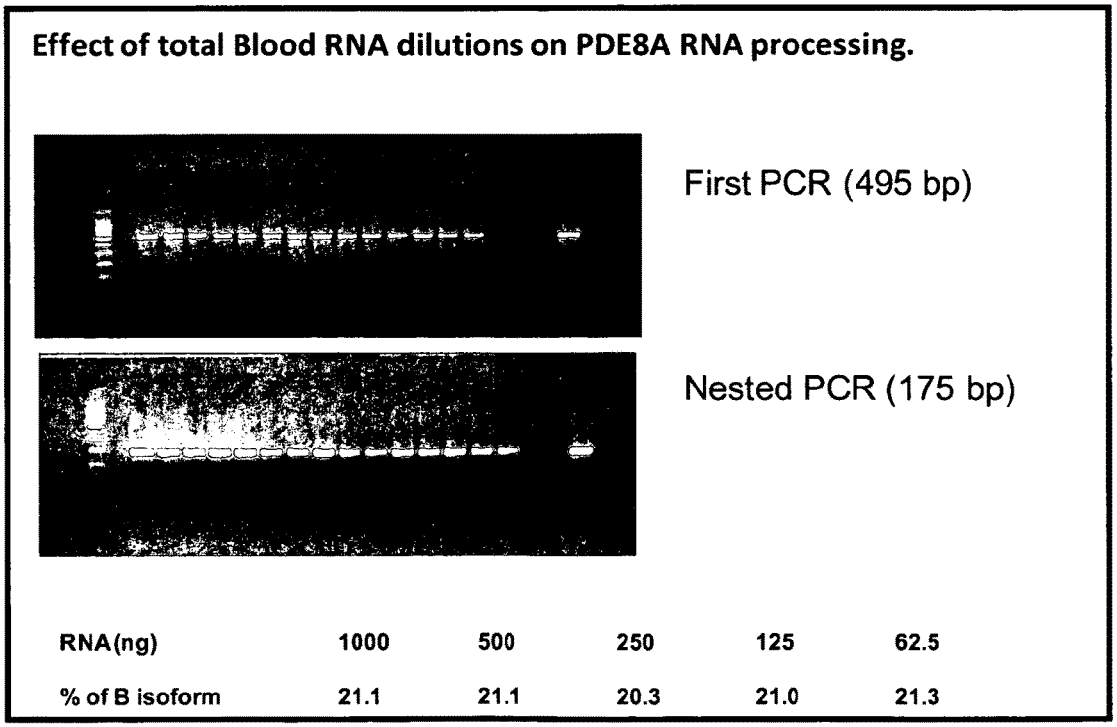

FIGURE 7

| Human Brain Cx | |
|---|---|
| Isoform | % |
| A | 4.0 |
| AB | 3.0 |
| ABG | 2.0 |
| B | 47.0 |
| BC | 12.0 |
| NE | 17.0 |
| SUM | 85.0 |

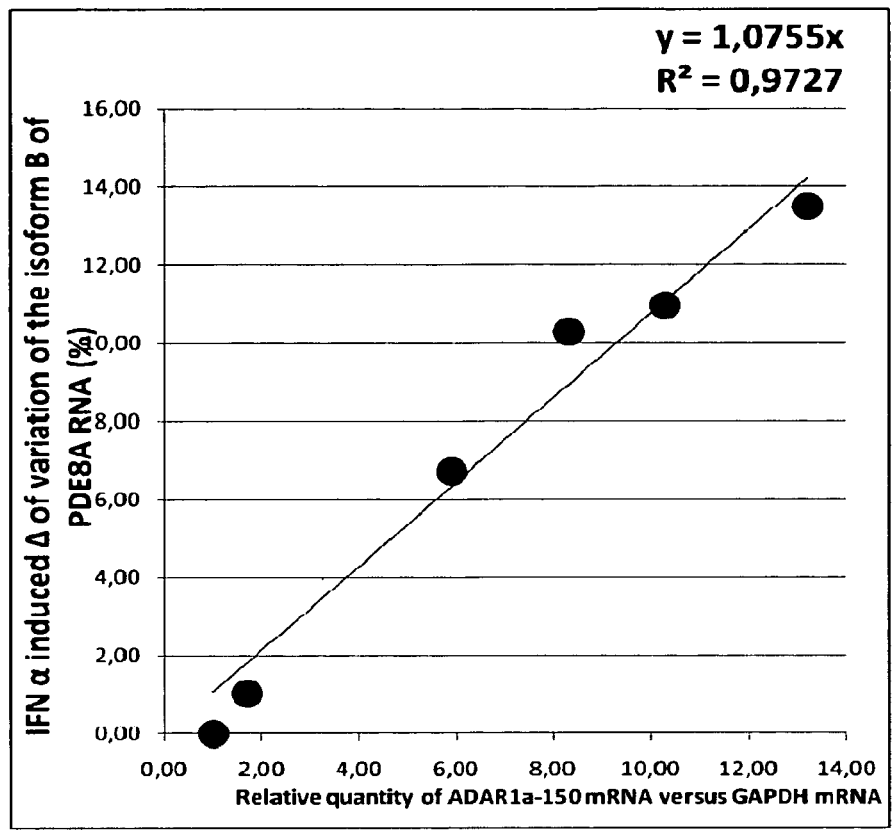

FIGURE 11

PDE8A-Intron 9 Editing Sites

Labelled primers used for PCR2 (175pb)

PDE8A-2FowFAM : 5'-CTAGGGAACCCTGTTTAGTCC-3' (SEQ ID NO. 11)

PDE8A-2RevVIC: 5'-CAATGGGCACCAAAAAAGGG-3' (SEQ ID NO. 12)

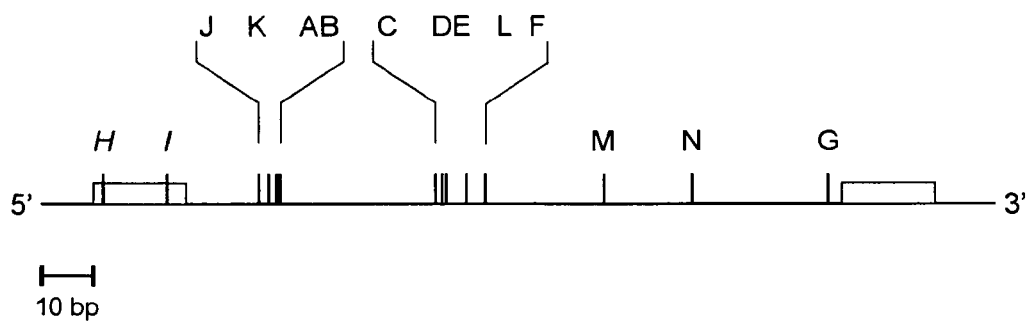

Comments: -Forward and reverse primers used for the second step of the nested PCR (fluorescent amplicon) are boxed in grey.
-Editing sites in italic (H and I) are *de facto* excluded from the CE-SSCP analyzis.
-A and B editing sites, like D and E sites are adjacent nucleotides of the intron sequence.

FIGURE 12

A

| Isoforms | % in DPFCx | SEM | % in ACCx | SEM | % in ERCx | SEM |
|---|---|---|---|---|---|---|
| B | 24,85 | 1,99 | 32,47 | 3,02 | 32,61 | 5,62 |
| ABC | 8,31 | 0,35 | 6,85 | 0,45 | 5,57 | 0,98 |
| Ne | 7,07 | 0,47 | 7,58 | 0,63 | 8,84 | 1,03 |
| BE | 5,44 | 0,12 | 5,37 | 0,19 | 4,24 | 0,59 |
| ABE | 4,82 | 0,34 | 4,52 | 0,33 | 3,89 | 0,60 |
| AB | 3,22 | 0,54 | 5,06 | 0,30 | 1,03 | 0,36 |

B

A

| Isoforms | % in controls (ACCx) | SEM | % in suicides (ACCx) | SEM |
|---|---|---|---|---|
| B | 32.47 | 3.02 | 25.88 | 1.93 |
| Ne | 7.58 | 0.63 | 8.56 | 0.53 |
| ABC | 6.85 | 0.45 | 6.12 | 0.47 |
| BE | 5.37 | 0.19 | 4.81 | 0.15 |
| AB | 5.06 | 0.30 | 5.90 | 0.30 |
| ABE | 4.52 | 0.33 | 5.08 | 0.26 |

B

```
                              SEQUENCE LISTING

<160> NUMBER OF SEQ ID NOS: 23

<210> SEQ ID NO 1
<211> LENGTH: 432
<212> TYPE: DNA
<213> ORGANISM: artificial
<220> FEATURE:
<223> OTHER INFORMATION: Partial sequence of intron 9 of the human PDE8A
      gene

<400> SEQUENCE: 1
ggttcttagt atattcacag ttttgcaaat gtcacaatta atttcccata ttccccttga        60
tagtgagctt tagaagtaac ccttagacct gtctgctgaa gccttccttc taaggtagac      120
atgcaagttg tggacatgga ggacaaccca cttatttctg cctagggaac cctgtttagt      180
ccttggtggc tttggactac aagcctcgtc ctgtgggctg agctcccct cagaactgta       240 ccaaggccca tacctccctt ctactccagt gtgacctaag gactcagctg ggctttctgg      300
ctgttttttg atatagccct tttttggtgc ccattgtttt cagaattata tcagtaagca      360
tcagtaatca tcctttgatt ctatcggagt attctggttt cttttttgatc tgctttccca    420 gaggagtctg aa                                                          432

<210> SEQ ID NO 2
<211> LENGTH: 432
<212> TYPE: DNA
<213> ORGANISM: artificial
<220> FEATURE:
<223> OTHER INFORMATION: Partial sequence of intron 9 of chimpanzee
      PDE8A gene

<400> SEQUENCE: 2
ggttcttagt atattcacag ttttgcaaat gtcacaatta atttcccata ttccccttga        60
tagtgagctt tagaagtaac ccttagacct gtctgctgaa gccttccttc taaggtagac      120
atgcaagttg tggacatgga ggacaaccca cttatttctg cctagggaac cctgtttagt      180
ccttggtggt tttggactac aagccttgtc ctgtgggctg agctcccct cagaactgta       240 ccaaggccca tacctccctt ctactccagt gtgacctaag gactcagctg ggctttctgg      300
ctgttttttg atatagccct tttttggtgc ccattgtttt cagaattata tcagtaagca      360
tcagtaatca tcctttgatt ctgttggagt attctggttt cttttttgatc tgctttccca    420 gaggagtctg aa                                                          432

<210> SEQ ID NO 3
<211> LENGTH: 424
<212> TYPE: DNA
<213> ORGANISM: artificial
<220> FEATURE:
<223> OTHER INFORMATION: Partial sequence of intron 9 of Macaca mulatta
      Rhesus monkey PDE8A gene

<400> SEQUENCE: 3
ggtttttagt atattcatgg ttttgcaaat gtcacaattt cccgtattcc ccttgatagt        60
```

```
gagcttcaga agtaacccct tagacctgtct cctgaagcct tccttctaag gtaggcatgc    120
aagttgtgga tatggagaac aacccactta tttctgccta gggaaccctg tttagtcctt    180
agcggttttg gactgccagc ctcgtcctct gggctgagct ccgcctcaga actgtactaa    240
ggcccatacc tcccttcttc tccagtgtga gctaaggact tagctgggct ttctggctgt    300
tttttgatat agccctttt ttggtgccca ttgttttcag aattaggaag catcagtaat    360
catcttttga ttctatcgga gtatcctggt ttcttttga tctgctttcc tagaggagtc    420
tgaa                                                                 424
```

```
<210> SEQ ID NO 4
<211> LENGTH: 800
<212> TYPE: DNA
<213> ORGANISM: artificial
<220> FEATURE:
<223> OTHER INFORMATION: Partial sequence of intron 9 of human PDE8A
      gene

<400> SEQUENCE: 4
ataaagaaag tatactattt ggtggttctt agtatattca cagttttgca aatgtcacaa     60
ttaatttccc atattcccct tgatagtgag ctttagaagt aacccttaga cctgtctgct    120
gaagccttcc ttctaaggta gacatgcaag ttgtggacat ggaggacaac ccacttattt    180
ctgcctaggg aaccctgttt agtccttggt ggctttggac tacaagcctc gtcctgtggg    240
ctgagctccc cctcagaact gtaccaaggc ccatacctcc cttctactcc agtgtgacct    300
aaggactcag ctgggctttc tggctgtttt ttgatatagc cctttttgg tgcccattgt    360 tttcagaatt atatcagtaa gcatcagtaa tcatcctttg attctatcgg agtattctgg    420 tttcttttg atctgctttc ccagaggagt ctgaagatga gctcttatca ttggtatttg    480
gatgcaggtt gccatgtacc aaacaagaat atttcagaat tgacctggag tagggctctg    540
gatagcaaac ctcagctaag ccaacaaggc tgccatggtg cttaacaccc agcctgggtc    600
aactctaggt cctgagggac tctggaaggc taagaaaggt tatggaatac cctaggggtt    660
cagtgtcctg ttgtgggttt tagggatttc catagtttaa gggccttggt gatttctttg    720
gaggaattca taacatttta ggacggtgac aaaacccagc tccatcctgg ctttccctac    780
caccccaaga taaagggagt                                                800
```

```
<210> SEQ ID NO 5
<211> LENGTH: 21
<212> TYPE: DNA
<213> ORGANISM: artificial
<220> FEATURE:
<223> OTHER INFORMATION: Primer PDE8A-RT

<400> SEQUENCE: 5
gtggtaggga aagccaggat g                                              21
```

```
<210> SEQ ID NO 6
<211> LENGTH: 22
<212> TYPE: DNA
<213> ORGANISM: artificial
<220> FEATURE:
<223> OTHER INFORMATION: Intron 9-specific forward primer

<400> SEQUENCE: 6
caacccactt atttctgcct ag                                             22
```

```
<210> SEQ ID NO 7
<211> LENGTH: 20
<212> TYPE: DNA
<213> ORGANISM: artificial
<220> FEATURE:
<223> OTHER INFORMATION: Intron 9-specific reverse primer

<400> SEQUENCE: 7
ttctgaaaac aatgggcacc                                              20

<210> SEQ ID NO 8
<211> LENGTH: 21
<212> TYPE: DNA
<213> ORGANISM: artificial
<220> FEATURE:
<223> OTHER INFORMATION: Intron 9-specific forward primer

<400> SEQUENCE: 8
gctgaagcct tccttctaag g                                            21

<210> SEQ ID NO 9
<211> LENGTH: 20
<212> TYPE: DNA
<213> ORGANISM: artificial
<220> FEATURE:
<223> OTHER INFORMATION: Intron 9-specific reverse primer

<400> SEQUENCE: 9
cctgggtcaa ctctaggtcc                                              20

<210> SEQ ID NO 10
<211> LENGTH: 21
<212> TYPE: DNA
<213> ORGANISM: artificial
<220> FEATURE:
<223> OTHER INFORMATION: PDE8A-2FowFAM primer

<400> SEQUENCE: 10
ctagggaacc ctgtttagtc c                                            21

<210> SEQ ID NO 11
<211> LENGTH: 20
<212> TYPE: DNA
<213> ORGANISM: artificial
<220> FEATURE:
<223> OTHER INFORMATION: PDE8A-2FRevVIC primer

<400> SEQUENCE: 11
caatgggcac caaaaaaggg                                              20

<210> SEQ ID NO 12
<211> LENGTH: 20
<212> TYPE: DNA
<213> ORGANISM: artificial
<220> FEATURE:
<223> OTHER INFORMATION: PDE8A-1REV primer

<400> SEQUENCE: 12
ggacctagag ttgacccagg                                              20

<210> SEQ ID NO 13
<211> LENGTH: 21
<212> TYPE: DNA
<213> ORGANISM: artificial
<220> FEATURE:
<223> OTHER INFORMATION: PDE8A-1FWD primer
```

```
<400> SEQUENCE: 13
gctgaagcct tccttctaag g                                           21

<210> SEQ ID NO 14
<211> LENGTH: 22
<212> TYPE: DNA
<213> ORGANISM: artificial
<220> FEATURE:
<223> OTHER INFORMATION: ADAR1-150 forward primer

<400> SEQUENCE: 14
gcctcgcggg cgcaatgaat cc                                          22

<210> SEQ ID NO 15
<211> LENGTH: 22
<212> TYPE: DNA
<213> ORGANISM: artificial
<220> FEATURE:
<223> OTHER INFORMATION: ADAR1-150 reverse primer

<400> SEQUENCE: 15
cttgcccttc tttgccaggg ag                                          22

<210> SEQ ID NO 16
<211> LENGTH: 24
<212> TYPE: DNA
<213> ORGANISM: artificial
<220> FEATURE:
<223> OTHER INFORMATION: ADAR1-110 forward primer

<400> SEQUENCE: 16
cgagccatca tggagatgcc ctcc                                        24

<210> SEQ ID NO 17
<211> LENGTH: 24
<212> TYPE: DNA
<213> ORGANISM: artificial
<220> FEATURE:
<223> OTHER INFORMATION: ADAR1-110 reverse primer

<400> SEQUENCE: 17
catagctgca tcctgcttgg ccac                                        24

<210> SEQ ID NO 18
<211> LENGTH: 23
<212> TYPE: DNA
<213> ORGANISM: artificial
<220> FEATURE:
<223> OTHER INFORMATION: ADAR2 forward primer

<400> SEQUENCE: 18
gctgcgcagt ctgccctggc cgc                                         23

<210> SEQ ID NO 19
<211> LENGTH: 23
<212> TYPE: DNA
<213> ORGANISM: artificial
<220> FEATURE:
<223> OTHER INFORMATION: ADAR2 reverse primer

<400> SEQUENCE: 19
gtcatgacga ctccagccag cac                                         23

<210> SEQ ID NO 20
<211> LENGTH: 24
```

```
<212> TYPE: DNA
<213> ORGANISM: artificial
<220> FEATURE:
<223> OTHER INFORMATION: 5-HT2CR forward primer

<400> SEQUENCE: 20
tgtccctagc cattgctgat atgc                                      24

<210> SEQ ID NO 21
<211> LENGTH: 24
<212> TYPE: DNA
<213> ORGANISM: artificial
<220> FEATURE:
<223> OTHER INFORMATION: 5-HT2CR reverse primer

<400> SEQUENCE: 21
gcaatcttca tgatggcctt agtc                                      24

<210> SEQ ID NO 22
<211> LENGTH: 26
<212> TYPE: DNA
<213> ORGANISM: artificial
<220> FEATURE:
<223> OTHER INFORMATION: 5-HT2CR forward primer

<400> SEQUENCE: 22
atgtgctatt ttcaacagcg tccatc                                    26

<210> SEQ ID NO 23
<211> LENGTH: 21
<212> TYPE: DNA
<213> ORGANISM: artificial
<220> FEATURE:
<223> OTHER INFORMATION: 5-HT2CR reverse primer

<400> SEQUENCE: 23
gcaatcttca tgatggcctt a                                         21
```

EDITING PROFILING OF PDE8A PRE-MRNA: USE AS SPECIFIC BIOMARKER OF ADARS ACTIVITIES IN HUMAN TISSUES TO DIAGNOSE AND TO PREDICT AND ASSESS THERAPEUTIC EFFICACY AND/OR EFFICIENCY OR POTENTIAL DRUG SIDE EFFECTS

CROSS-REFERENCE TO RELATED APPLICATIONS

This application is a continuation of U.S. application Ser. No. 16/442,825, filed on Jun. 17, 2019, now U.S. Pat. No. 10,851,420, which is a division of application Ser. No. 15/479,648, filed on Apr. 5, 2017, now U.S. Pat. No. 10,323,283, which is a continuation of application Ser. No. 13/959,928, filed on Aug. 6, 2013, now abandoned, which is a continuation of application Ser. No. 13/805,902, filed as application No. PCT/EP2011/060644 on Jun. 24, 2011, now abandoned, which claims the benefit of priority from U.S. Provisional Application No. 61/344,298, filed on Jun. 24, 2010, all of which are incorporated by reference in their entireties.

The present invention relates to the use of the editing profile of PDE8A pre-mRNA as a specific biomarker of ADARs activities in evolved primate, particularly in Human tissues. The present invention also relates to an in vitro method for predicting in Human an alteration of the mechanism of the ADARs catalysed pre-mRNA editing of target genes, by analysing the PDE8A pre-mRNA editing profile in a peripheral tissue sample containing cells expressing said PDE8A pre-mRNA, such as blood sample. The present invention is also directed to an in vitro method for the screening of potential therapeutic compounds and to predict and assess therapeutic efficacy and/or efficiency or to diagnose potential severe brain or peripheral drug side effects implementing said PDE8A pre-mRNA editing profile as specific biomarker. The present invention is further directed to a method for determining the PDE8A pre-mRNA editing profile in Human, particularly by capillary electrophoresis single-strand conformation polymorphism (CE-SSCP) method after amplification by a nested PCR. Finally the invention relates to particular nucleic acid primers implemented in said nested PCR and kit comprising such sets of primers and human cells capable of expressing PDE8A and ADARs. Alternatively, PDE8A pre-mRNA editing profiling in Human could be carried out by ultra high-throughput sequencing (HTS) technologies. Abbas and collaborators in one hand, and Morabito and collaborators in the other have recently developed editing quantification applications for the HTS Illumina technology (Abbas et al., 2010, Nucl. Acid Res.; Morabito et al., 2010, Mol. Pharmacol.)(see material and methods sections of the cited articles). These approaches have been set up for 5-HT2cR mRNA editing quantification in the mouse brain. The results presented by the authors are very close to those described by Poyau and collaborators in their princeps paper (Poyau, 2007). With some modifications of the design of primers used for cDNA amplification (second nested PCR), and of the size of the generated amplicons, the Illumina technology could also be applied to PDE8A pre-mRNA editing analyzis. Similarly the HTS Ion Torrent semiconductor sequencing technology (Life technologies) based on direct electrical detection of DNA synthesis could be used for PDE8A pre-mRNA editing profile quantification (Pourmand et al., 2006. Proc. Natl. Acad. Sci.; Anderson et al., 2008, Sens. Actuators B. Chem.). Whatever the method used, the starting material would remain the cDNA libraries built from total RNAs and the first PCR products described in the material and methods of this patent.

Adenosine (A) to Inosine (I) RNA editing is accepted as a fundamental post transcriptional mechanism of control of a large population of functional proteins. Due to the activities of specific enzymes (ADARs) it can control a large set of targets (1). It implicates the formation of pre-mRNAs double stranded structures on which specific edited sites have been identified. These Adenosines can belong to a coding sequence (eg: 5-HT2c receptor (5HT2CR), Glutamate receptor) (2, 3) or an intronic sequence (Phosphodiesterase subtype 8A (PDE8A)(4, 5). In this later configuration the editing process could influence both the RNA splicing pattern and/or the formation of different isoforms of miR-NAs (6). The observed modifications of sequences due to the editing can thus be due to modifications of the relative concentrations of the different ADARs at the editing processing site, and/or to an alteration of the efficiency of the editing enzymes themselves. Previous studies have clearly indicated that both types of mechanisms could be at the origin of specific pathological or pharmacological alterations (7, 5).

The invention presents the rapid and quantitative onset of the editing profile of PDE8A pre-mRNA as a strongly efficient tools to predict significant alterations of the activities of ADARs in total RNA extracts of Human tissues including Brain and of more easily accessible blood samples. Genetic observations indicate that the rapid solution of this genomic approach opens new possibilities to evaluate primary or secondary risks of severe psychiatric drug induced side effects.

The PDE8A gene is located on chromosome 15q25.3 (Ensemble Genome browser). A genome scan using 297 families with proband who had recurrent early-onset major depressive disorder (MDD) observed significant evidence for linkage on chromosome 15q25.3-q26.2 (8). The authors confirmed this genetic association in their final report (9). The most significant scores were observed for the markers D15S652 and GATA128A02. An independent genome scan of 497 sib pairs with recurrent depression found a modest signal for linkage at the same position on chromosome 15q, with the most significant marker (D15S1047) located approximately 11 Mb proximal to D15S652 (10). Another genome scan, using pedigrees with recurrent early-onset depression and anxiety disorders, found suggestive evidence for linkage to 15q in this same region (11). Further association studies trying to ascribe to the NTRK3 gene (located approximately 5 Mb proximal to D15S652) a role in MDD were not fully convincing (11, 12). The authors suggest that this gene is probably not a major contributor to the overall risk for depression.

Recently, a meta-analysis of 3 European-ancestry MDD genome-wide association study data sets was carried out by Shyn and collaborators (Shyn et al., 2011, Mol. Psychiatry). The data sets totalized 3957 cases and 3428 controls. Among several candidates, the authors found that SNP rs11634319 (chr15: 84,224,912) located in band 15q25.3 in the vicinity of the PDE8A gene was associated to a female-narrow phenotype of major depression ($p<10^{-5}$).

On the other hand, older experiments conducted by Aston and collaborators, had compared gene expression in the temporal cortex from 12 patients with major depressive disorder and 14 matched controls by using Affimetrix microarrays (Aston et al., 2005, Mol. Psychiatry). Significant expression changes were identified in families of genes involved in neurodevelopment, cell communication and signal transduction. Among the latter family, the mRNA abundance of the PDE8A gene was twofold less in depressed people (p<0.0003). This result was highly significant as the PDE8A mRNAs were detected in all controls and patients unlike messengers of other genes. All these linkage, association, and microarray gene expression studies tend to indicate that the PDE8A gene could be associated to major depression disorder.

Using an original method based on glyoxilated poly(A)+ RNA treated by RNasc T1, Morse and collaborators have identified new targets of the editing enzymes ADARs in the Human brain (4). They showed that non-coding regions of pre-mRNA (introns, 3'UTR) appear to be the primary targets of ADARs. Intron 9 of the PDF8A gene (13) (PDE8A gene imbedded in contig NT_010274) coding for a c-AMP specific phosphodiesterase is one of these targets. Recently, in the scope of systemic autoimmune lupus erythematosus disorder, and in T-lymphocytes, Orlowski and collaborators have observed two hot spots for A to I editing in PDE8A gene transcripts (5). The first one, called site 1, concerned two adenosine residues at positions 5505 and 5506 of intron 9. We called these editing sites A and B, respectively. The second hot spot or site 2 concerned three other adenosines at positions 5536, 5538 and 5539 of intron 9. These editing sites were called C. D and E, respectively. Low frequency sites of editing were also observed at base positions 5468, 5548 and 5617 of intron 9 of gene PDE8A (editing sites H, F and G, respectively). All these editing sites, embedded in their sequence contexts are shown in FIG. 1.

The 2D structure of RNA sequence corresponding to base positions 5367 to 5736 of intron 9 of gene PDE84 is presented in FIGS. 2 and 3. Only editing sites A. B, F, G and H are embedded in stem structures, C, D and E are in a loop.

There is a need to provide with in vitro tests which can rapidly determine the activity of the ADARs, particularly a specific biomarker of these ADARs activities in Human tissues easy to analyse. Such tests will allow the demonstration of alteration of the ADARs catalysed-pre-mRNA editing mechanism.

A platform implementing such a specific ADARs biomarker activities could be proposed to evaluated, for example at a pre-clinical stage, the potential effect of new therapeutic molecules on the editing regulation associated to this ADARs catalyzed—pre-mRNA editing mechanism since editing has been already found altered in patients suffering from depression or having committed suicide. Moreover, such a specific ADARs biomarker activities could be also proposed for rapid, effective methods by which we can diagnose in patients pathologies associated to the alteration of this editing mechanism or by which we can determine the potential toxicity of efficiency of test compounds, or potential side-effects profile of a drug in man, particularly before the post-marketing period. There is also a need for tools and kits for the implementation of such methods.

This is the object of the present invention.

The inventors have demonstrated that editing alterations produced by increasing concentrations of IFNα applied to SH-SY5 Y human cells could influence the steady state of PDE8A protein isoforms. They have thus observed after a western blot analysis of the PDE8A proteins concentrations in the SH-SY5 Y cells, that the concentration of PDE8A4 isoform of the protein could be significantly ($R^2$=0.82) and negatively linearly correlated (slope=−3.6) with the positive Δ of variation of the RQ versus GAPDH of the ADAR1a-p150 induced by IFNα application during 24 hours. The best fitting of the effect versus concentrations of IFNα led to an estimated EC 50% of 3.3 f 4.4 (SD) IU/ml with a $R^2$ of the fit=0.7 and a corresponding maximal effect of −47% of the steady state concentration found in controls.

This example demonstrates that the editing process would precisely control the expression of the PDE8A proteins either by its possible influence on the splicing mechanism or by the control of the sequence of dedicated miRNAs.

Moreover, the major interest of this specific editing target is that it is present particularly in the Human Blood as in brain which is not the case of 5-HT2CR. The editing profile of PDE8A can be thus considered as a specific tool to evaluate the activity of the editing enzymes machinery in human tissues including blood.

Together to the analysis of the complete editing profile of the PDE8A in evolved primate including Human, the inventors have demonstrated that an evaluation of the expression of the editing profile of the PDE8A pre-mRNA as a complementary approach is particularly well adapted to the evaluation of the general editing context of dysregulation of the editing machinery. It includes the quantitative and qualitative analysis of the editing profile of the PDE8A pre-mRNA (particularly by quantitative nested RT-PCR associated to a CE-SSCP method).

The examples below strongly support the interest of measuring the editing process of this specific target as an innovative tool in various preclinical and clinical investigations.

Thus, the present invention is directed to a method in vitro for the determination of the ADARs (Adenosinc Dcaminase, RNA-specific) activity comprising the following steps of:
a) obtaining a biological sample containing mammal cells wherein said mammal cells express the editing enzymes ADAR1a, ADAR1b and ADAR2 and the phosphodiesterase subtype 8A (PDE8A);
b) determining in a cellular extract the editing profile of the PDE8A pre-mRNA measured in a cellular RNA extract obtained from said cellular extract, preferably said editing profile giving the mean proportion of each identified isoform of the PDE8A pre-mRNA;
c) comparing the profile obtained in step b) between said mammals cells with the PDE8A pre-mRNA editing profile obtained for control cells whose ADARs activity is known.

In another aspect, the present invention is directed to an in vitro method for identifying in vitro or to diagnose whether a patient presents a pathology or is at risk to develop a pathology related to an alteration of the ADARs catalyzed pre-mRNA editing mechanism, wherein this method comprising the following steps of:
a) obtaining from the patient to be tested a biological sample containing cells wherein said cells express the editing enzymes ADAR1a, ADAR1b and ADAR2 and the PDE8A, preferably a biological sample containing PBMC (Peripheral Blood Mononuclear Cells);
b) determining the editing profile of the PDE8A pre-mRNA measured in a cellular RNA extract obtained from said biological sample containing cells, preferably said editing profile giving the mean proportion of each identified isoform of the PDE8A pre-mRNA;
c) identifying whether said patient presents or is at risk to develop such a pathology by comparing the editing profile of the PDE8A pre-mRNA obtained in step b) with control editing profile of the PDE8A pre-mRNA obtained for normal patients and/or for patients exhibiting pathologies related to an alteration of the mechanism of this mRNA editing.

In a preferred embodiment, a significant difference between the editing profiles of the PDE8A pre-mRNA measured between the control sample and the tested patient sample is indicative of the presence of such a pathology or a risk for such a pathology.

By significant difference, it is intended to designate a difference of at least 2%, preferably at least 3%, 4%, 5%, 6%, 7%, 8%, 9% and 10% between the tested patient cells and the control cells for at least one of the same isofbrm (edited or non edited isoform), more preferably this at least one of the same isoform being selected from the group of the AB, ABC, ABE, ABEF, ABEFG, ABG, B, BC, BD, BE, BEG, BF, BFG, BG, M or the non edited isoform (ned or ne or Ne), the most preferred being the B, AB, BC, ABC and ned isoform.

In a more preferred embodiment, by significant difference, it is intended to designate a difference of at least 2%, preferably at least 3%, 4%, 5%, 6%, 7%, 8%, 9% and 10% between the tested patient cells and the control cells for at least a same pair of isoforms (edited or non edited isoform), more preferably this at least same pair of isoforms being selected from the group of the AB, ABC, ABE, ABEF, ABEFG, ABG, B, BC, BD, BE, BEG, BF, BFG, BG, M edited isofonms and the non edited isoform (ned), the most preferred being a same pair selected in the group consisting of the B, AB, BC, ABC and ned isoforms, B and ned isoforms being the most preferred pair of isoforms.

In another aspect, the invention is directed to an in vitro method for monitoring the efficacy of a therapeutic treatment in a patient having a pathology or at risk to present a pathology related to an alteration of the ADARs catalyzed pre-mRNA (or mRNA) editing mechanism, said method comprising the step of:
   a) obtaining a biological sample from said patient before the treatment and at least after one interval during said treatment and wherein said biological sample contains cells, said cells expressing the editing enzymes ADAR1a, ADAR1b and ADAR2 and PDE8A;
   b) determining in a cellular extract from said biological sample the editing profile of the PDE8A pre-mRNA measured in a cellular RNA extract obtained from said cellular extract, preferably said editing profile giving the mean proportion of each identified isoform of the PDE8A pre-mRNA;
   c) comparing the results obtained in step b) between said biological sample cellular extract obtained from the patient before and after said interval during the treatment.

In a preferred embodiment, a non-significant modification of said PDE8A pre-mRNA editing profile measured after said interval during the treatment is indicative of a lack efficacy of the therapeutic treatment.

In an also preferred embodiment, the obtaining of a PDE8A pre-mRNA editing profile measured after said interval having significantly the same profile obtained for biological sample controls from subjects who do not present or who are not at risk to present a pathology related to an alteration of the ADARs catalyzed pre-mRNA (or mRNA) editing mechanism, is indicative of an efficacy of the treatment.

In another aspect, the present invention comprises a method in vitro for the determination of the potential toxicity or side-effects of a test compound after its administration in a patient and wherein said compound is tested for its ability to prevent or to treat a pathology directly or indirectly related to an alteration of the ADARs catalyzed pre-mRNA (or mRNA) editing mechanism comprising the following steps of:
   a) obtaining a biological sample containing mammal cells wherein said mammal cells express the editing enzymes ADAR1a, ADAR1b and ADAR2 and the phosphodiesterase subtype 8A (PDE8A);
   b) contacting said mammals cells with the compound to be tested;
   c) determining in a cellular extract the editing profile of the PDE8A pre-mRNA measured in a cellular RNA extract obtained from said cellular extract, preferably said editing profile giving the mean proportion of each identified isoform of the PDE8A pre-mRNA;
   d) comparing the results obtained in step c) between said treated cells with the compound to be tested obtained in step b) and non treated control cells.

In the context of the invention, the term "toxicity" refers to any adverse and/or side effect of a compound on the metabolism of a cell or a tissue and more generally any alteration in metabolism that can result in a harmful effect of the compound on the patient, particularly in the context of the present invention the potential risk of drug induced mood disturbance and suicide.

The term "test compound" refers in general to a compound to which a test subject is exposed. Typical test compounds will be small organic molecules, typically drugs and/or prospective pharmaceutical lead compounds, but can include proteins, peptides, polynucleotides, heterologous genes (in expression systems), plasmids, polynucleotide analogs, peptide analogs, lipids, carbohydrates, viruses, phage, parasites, and the like.

The term "control compound" refers to a compound that is not known to share any biological activity with a test compound, which is used in the practice of the invention to contrast "active" (test) and "inactive" (control) compounds during the derivation of Group Signatures and Drug Signatures. Typical control compounds include, without limitation, drugs used to treat disorders distinct fmm the test compound indications, vehicles, inactivated versions of the test agent, known inert compounds, and the like.

In another aspect, the present invention encompasses a method in vitro for the selection of a therapeutical compounds useful for the treatment of pathology related to an alteration of the ADARs catalyzed pre-mRNA (or mRNA) editing mechanism (ADAR dependent A to I pre-mRNA editing mechanism) comprising the following steps of:
   a) obtaining a biological sample containing mammal cells wherein said mammal cells express the editing enzymes ADAR1a, ADAR1b and ADAR2 and PDE8A;
   b) contacting said mammals cells with the compound to be tested;
   c) determining in a cellular extract the editing profile of the PDE8A pre-mRNA measured in a cellular RNA extract obtained from said cellular extract, preferably said editing profile giving the mean proportion of each identified isoform of the PDE8A pre-mRNA;
   d) comparing the results obtained in step c) between said treated cells with the compound to be tested and non treated control cells.

In a preferred embodiment of the methods of the present invention in step b) said mammals cells are cultured in presence of the compound to be tested in a medium suitable or convenient for the culture of said mammal cells.

Preferably, in step b) said mammals cells are cultured in presence of the compound to be tested for at least the time necessary to modify the expression of edited isoforms of PDE8A pre-mRNA and/or the ADAR1a, ADAR1b and ADAR2 enzymes expressed, whether they can be modified by such a compound.

Preferably in step b) said mammals cells are cultivated in presence of the compound to be tested for at least 1 hour, more preferably at least 5, 10, 24 or 48 hours before the step c) of determining in the same cellular extract the editing profile of each identified isoform of the PDE8A pre-mRNA and/or the quantitative expression of said editing enzymes ADAR1a, ADAR1b and ADAR2.

In a preferred embodiment of the methods of the present invention the compound to be tested is further administered in vivo to an evolved primate animal model, suitable to test the same compound and wherein the potential toxicity or side-effects of this test compound after its administration in this animal model can be evaluated, particularly by evaluating the alteration of the pre-mRNA editing of the PDE8A and/or the ADAR isoforms expressed in total blood, particularly PBMC, or in brain.

In a preferred embodiment, in addition to the determination of the editing profile of the PDE8A pre-mRNA measured in a cellular RNA extract in step b) or c) of the methods according to the invention, these steps further comprises the determination of the quantitative expression of said editing enzymes ADAR1a, ADAR1b and ADAR2 in a cellular extract of said cells.

The step of comparing the results obtained in step c) or d) further comprises the comparison of the results obtained between the treated cells and non treated control cells for ADAR expression.

In a preferred embodiment, the editing profile of the PDE8A pre-mRNA measured in the cellular RNA extract and the quantitative expression of said editing enzymes ADAR1a, ADAR1b and ADAR2 are determined in the same cellular extract.

In an also preferred embodiment, the quantitative expression of said editing enzymes ADAR1a, ADAR1b and ADAR2 is determined by the measure of the mRNA expression of said editing enzymes or by the measure of said editing enzymes protein expressed in the cellular extract.

In another preferred embodiment, the quantitative expression of said editing enzymes ADAR1a, ADAR1b and ADAR2 is determined by the measure of the mRNA expression of said editing enzymes, preferably determined in the same total RNA cell extract used for the determination of the editing profile of the PDE8A pre-mRNA.

In another preferred embodiment, said mammal cells capable of expressing the ADARs isotypes ADAR1a, ADAR1b and ADAR2, and the PDE8A are from an evolved primate, such as chimpanzee, Rhesus macaque or Human.

In another preferred embodiment, said mammal cells are human cells or human derived cells such as cells derived from human cell line or recombinant cells originating from human cell line.

In method according to one of claims 1 to 12, wherein in step a), said mammal cells capable of expressing the ADARs isotypes ADAR1a, ADAR1b and ADAR2, and the PDE8A are from a biological sample of a subject or a patient selected from the group of biological samples consisting in blood samples (PBMC) or body fluids (LCR) or preoperative and post mortem tissues (brain, liver, prostate) or biopsy samples (skin, tumors).

In another preferred embodiment, said mammal cells capable of expressing the ADARs isotypes ADAR1a, ADAR1b and ADAR2, and the PDE8A are from a biological sample containing cells derived from a cell line.

In another preferred embodiment, said mammal cells capable of expressing the ADARS isotypes ADAR1a, ADAR1b and ADAR2, and the PDE8A are from a biological sample containing cells derived from a cell line selected from the group consisting of evolved primate neuroblastoma, glioblastoma, astrocytoma and other tissue or tumor specific cell lines, preferably from the human neuroblastoma SH-SY5 Y cell line.

In another preferred embodiment, said mammal cells capable of expressing the ADARs isotypes ADAR1a, ADAR1b and ADAR2, and the PDE8A are from a biological sample containing cells derived from a recombinant cell line, optionally transformed by a vector carrying a nucleic acid encoding for at least one of an evolved primate ADARs isotypes selected from ADAR1a, ADAR1b and ADAR2 isotypes, or an evolved primate PDE8A.

In a preferred embodiment, said pathology related to an alteration of the ADARs catalyzed pre-mRNA editing mechanism, is a pathology selected from the pathologies related to an alteration of:
  the ADARs catalyzed 5-HT2c receptor (5-HT2CR) mRNA editing mechanism;
  the ADARs catalyzed GluR-B receptor pre-mRNA editing mechanism;
  the ADARs catalyzed K(V)1·1 potassium channel mRNA editing mechanism,
  the ADARs catalyzed FlnA or Blcap, (Riedmann et al; RNA 2008. 14: 1110-1118 Li et al; Science 2009 324,1210)) mRNA editing mechanism;
  ADARs catalyzed viral RNAs after infection mRNA editing mechanism.

In a more preferred embodiment, wherein said pathology related to an alteration of the ADARs catalyzed pre-mRNA (or mRNA) editing mechanism is selected from the group consisting of psychiatric, neurological, immunological and degenerative syndromes associated to an alteration of PDE8A intronic A to I pre-mRNA editing When said pathology is related to the ADARs catalyzed 5-HT2C receptor mRNA editing mechanism is selected from the group consisting of mental disorders, schizophrenia, depression, Bipolar disease, suicide or abnormal feeding behaviour (obesity, anorexia), but also Mild Cognitive Impairment (MCI), Epilepsia, Alzheimer or Chronical pain syndromes.

When said pathology is related to the ADARs catalyzed GluR-B receptor mRNA editing mechanism is selected from the group consisting in MCI, Epilepsia, Alzheimer, Amyotrophic Lateral Sclerosis (ALS) (Hideyama et al, 2010, J Pharmacol. Sci. 113, 9-13).

Additionally, related to ADAR1 genetic alterations the Dyschromatosis symetrica hereditaria (Suzuki et al., 2007, J invest. Dermatol. 309-311 In another aspect, said mammals cells implemented in the methods of the present invention further express the 5-HT2CR and, in addition to the determination of the editing profile of the PDE8A pre-mRNA measured in a cellular RNA extract in step b) or c) of the methods according to the invention, and, optionally comprising the determination of the quantitative expression of the editing enzymes ADAR1a, ADAR1b and ADAR2 in a cellular extract of said cells, this step further comprises the determination of the editing profile of the 5-HT2CR mRNA, preferably by the CE-SSCP method already described for the determination of the editing profile of the 5-HT2CR mRNA in human samples in the patent document PCT/EP 2008/057519 filed on Jun. 13, 2008 and the patent document PCT/EP2009/067464 filed on Dec. 17, 2009.

When the editing profile of the 5-HT2CR mRNA is also determined, the step of comparing the results obtained in step c) or d) further comprises the comparison of the results obtained between the treated cells and non treated control cells for the editing profile of the 5-HT2CR mRNA.

In a preferred embodiment, the editing profile of the PDE8A pre-mRNA measured in a cellular RNA extract obtained from said cellular extract, preferably said editing profile giving the mean proportion of each identified isoform of the PDE8A pre-mRNA comprises at least the determination and/or the quantification of the edited sites: A, B, C, D, E, F, G, H, I, J, K, L, M, N, or at least one of the PDE8A pre-mRNA isoforms comprising at least one of the editing sites A, B, C, D, E, F, G, H, I, J, K, L, M, N additionally with the non edited isoform (ned).

In a more preferred embodiment, the editing profile of the PDE8A pre-mRNA measured in a cellular RNA extract obtained from said cellular extract, preferably said editing profile giving the mean proportion of each identified isoform of the PDE8A pre-mRNA comprises at least the determination and/or the quantification of the PDE8A pre-mRNA isoforms AB, ABC, ABE, ABEF, ABEFG, ABG, B, BC, BD, BE, BEG, BF, BFG, BG, M or the non edited isoform (ned).

In an also more preferred embodiment, the editing profile of the PDE8A pre-mRNA measured comprises at least the determination and/or the quantification of the isoform B or at least one of the PDE8A pre-mRNA isoforms comprising at least the editing site B edited.

In an also more preferred embodiment, the editing profile of the PDE8A pre-mRNA measured comprises at least the determination and/or the quantification of the isoforms (ned).

In an also more preferred embodiment, the editing profile of the PDE8A pre-mRNA measured comprises at least the determination and/or the quantification of the isoforms ned and B, preferably at least (ned), B an AB, more preferably at least (ned), B, AB and BC.

In a preferred embodiment of the method according to the present invention, the editing rate for each edited and unedited form of said PDE8A pre-mRNA is determined by a method which comprises the following steps:
  A) extraction of the total RNAs of said mammal cells, followed, where appropriate, by purification of the pre-mRNAs;
  B) reverse transcription of the RNAs extracted in step A); and
  C) PCR amplification of the cDNAs obtained in step B) using at least a pair of primers specific for the PDE8A pre-mRNA fragment containing the edition sites which may be edited, this pair of primers being chosen so as to be able to amplify all the editing forms and the unedited form potentially present in the RNA extract.

In a preferred embodiment of the method according to the present invention, the editing rate for each edited and unedited form of said PDE8A pre-mRNA is determined by a method which comprises the following steps:
  A) extraction of the total RNAs of said mammal cells, followed, where appropriate, by purification of the pre-mRNAs;
  B) reverse transcription of the RNAs extracted in step A); and
  C) PCR amplification of the cDNAs obtained in step B) using at least a pair of primers specific for the PDE8A pre-mRNA fragment containing the edition sites which may be edited, this pair of primers being chosen so as to be able to amplify all the editing forms and the unedited form potentially present in the RNA extract, and wherein the step B) of reverse transcription is carried out by using an oligonucleotidic primer specific of the PDE8A gene.

In a preferred embodiment of the method according to the present invention, in step C), the primers used in the PCR amplification step (in the second round if it is a nested type PCR) are labelled, preferably labelled with fluorophores.

In a preferred embodiment of the methods of the present invention in step c), the editing profile giving the mean proportion of each identified isoform of the PDE8A pre-mRNA is determined by an SSCP method capable of providing the editing profile for each of the edited and unedited separate forms of said pre-mRNA, said SSCP method being characterized in that it comprises after the steps A). B) and C) the following steps:
  D) where appropriate, purification of the PCR products obtained in step C);
  E) where appropriate, quantification of the PCR products obtained in step D);
  F) dissociation of the double-stranded cDNAs to single-stranded cDNAs, in particular by beating followed by abrupt cooling;
  G) separation of the single-stranded cDNAs by capillary electrophoresis; and
  H) obtaining of the editing profile by reading of the fluorescence and, where appropriate, acquisition of the profile data by means of the exploitation system associated with the fluorescence reader.

In a particular preferred embodiment, the editing profile, preferably the editing profile giving the mean proportion of each identified isoform, of the PDE8A pre-mRNA measured in the cellular RNA extract of evolved primate cells, preferably human, is measured by RT followed by a nested type PCR comprising two rounds of PCR, and wherein:
  a) the first round of PCR is carried out by the following sets of primers:
Forward:

```
PDE8A-1FWD
                    (SEQ ID NO. 13)
GCTGAAGCCTTCCTTCTAAGG
```

Reverse:

```
PDESA-1REV
                    (SEQ ID NO. 12)
GGACCTAGAGTIGACCCAGG
``` and wherein
  b) the second round of PCR is carried out by the following set of primers:
Forward:

```
PDE8A-2FowFAM
                    (SEQ ID NO. 10)
CTAGGGAACCCTGTTTAGTCC
```

Reverse:

```
PDE8A-2Rev VIC
                    (SEQ ID NO. 11)
CAATGGGCACCAAAAAAGGG
```

When ADARs specific isoforms have to be determined in the method, it is preferred that the pair of primers specific for the evolved primate, preferably human, ADAR mRNA PCR amplification are selected from the group consisting of:

for ADAR1-150 isoform mRNA amplification:

```
Forward:
                                       (SEQ ID NO. 14)
5'-GCCTCGCGGGCGCAATGAATCC-3'

Reverse:
                                       (SEQ ID NO. 15)
5'-CTTGCCCTTCTTTGCCAGGGAG-3'
``` for ADAR1-110 isoform mRNA amplification:

```
Forward:
                                       (SEQ ID NO. 16)
5'-CGAGCCATCATGGAGATGCCCTCC-3'

Reverse:
                                       (SEQ ID NO. 17)
5'-CATAGCTGCATCCTGCTTGGCCAC-3'
``` for ADAR2 mRNA amplification:

```
Forward:
                                       (SEQ ID NO. 18)
5'-GCTGCGCAGTCTGCCCTGGCCGC-3'

Reverse:
                                       (SEQ ID NO. 19)
5'-GTCATGACGACTCCAGCCAGCAC-3'
```

In a more preferred embodiment of the method according to the present invention, the quantification of the editing profiles of PDE8A pre-mRNA including separation and identification of each of the isoforms is carried out by capillary electrophoresis single strand conformation polymorphism (CE-SSCP).

In a particular preferred embodiment, the method of the present invention further comprises a step of determining the quantity of the PDE8A mRNA expressed in said mammal cell by a Q-PCR or a step of determining the quantity of the PDE8A polypeptide expressed in said mammal cell.

In a preferred embodiment of the methods of the present invention in step b) or c), when the editing profile of the 5-HT2CR mRNA, preferably giving the mean proportion of each identified isoform of the 5-HT2CR mRNA measured in the cellular RNA extract, is determined, said determination is carried out by a nested type PCR comprising two rounds of PCR, and wherein the first round of PCR is carried out by the following sets of primers:

```
Forward:
                                       (SEQ ID NO. 20)
5'-TGTCCCTAGCCATTGCTGATATGC-3', Reverse:
                                       (SEQ ID NO. 21)
5'-GCAATCTTCATGATGGCCTTAGTC-3';
``` and wherein the second round of PCR is carried out by the following set of primers:

```
Forward:
                                       (SEQ ID NO. 22)
5'-ATGTGCTATTTTCAACAGCGTCCATC-3', Reverse:
                                       (SEQ ID NO. 23)
5'-GCAATCTTCATGATGGCCTTA-3'.
```

In another aspect, the present invention is directed to a kit for the determination of the editing profile of the PDE8A pre-mRNA comprising:

a) the following set of primers:

```
                                       (SEQ ID NO. 13)
         GCTGAAGCCTTCCTTCTAAGG (SEQ ID NO. 12)
         GGACCTAGAGTTGACCCAGG
``` and b) the following set of primers, preferably labelled:

```
                                       (SEQ ID NO. 10)
         CTAGGGAACCCTGTTTAGTCC (SEQ ID NO. 11)
         CAATGGGCACCAAAAAAGGG
```

The present invention also relates to a kit for the determination of the editing profile of the PDE8A pre-mRNA comprising:

a) mammal cells from evolved primate cell line, preferably human cell line, wherein said cells express the editing enzymes ADAR1a, ADAR1b and ADAR2 and the PDEA8, optionally the serotonin 2C receptor (5HTR2C); and b) two set of primers for determining by a RT/PCR involving a nested type PCR comprising two rounds of PCR the editing profile of the PDE8A pre-mRNA which can be present in a RNA extract of said mammal cells; and/or c) optionally a set of primers for measuring by a quantitative Q-PCR the quantitative expression of the editing enzymes ADAR1a, ADAR1b and ADAR2 and the level of expression of the PDE8A mRNA by using the following set of primers (Applied Biosystems references):

PDE8A1 Hs 01079628_m1
PDE8A Hs 00400174_m1

In a preferred embodiment, said mammal cells are from an evolved primate tumor cell line, such as neuroblastoma, glioblastoma or astrocytoma cell line, preferably from a human neuroblastoma cell line, more preferably the human neuroblastoma SH-SY5 Y cell line.

In a more preferred embodiment the two sets of primers of b) in the kit of the invention are:

a) the following set of primers:

```
                                       (SEQ ID NO. 13)
         GCTGAAGCCTTCCTTCTAAGG (SEQ ID NO. 12)
         GGACCTAGAGTTGACCCAGG
``` and b) the following set of primers, preferably labelled:

```
                                       (SEQ ID NO. 10)
         CTAGGGAACCCTGTTTAGTCC (SEQ ID NO. 11)
         CAATGGGCACCAAAAAAGGG
```

Finally, in a particular aspect, the present invention is directed to an in vitro method for the determination or for the prediction of the potential toxicity or side-effects of a interferon alpha (IFNα) treatment after its administration in a patient, particularly for a patient infected by the HCV (Hepatitis C virus), said method comprising the following steps of:
- a) obtaining a biological sample containing mammal white cells, preferably PBMC cells, from said treated patient;
- b) determining in the cellular extract of said biological sample containing mammal white cells the quantitative expression of the editing profile of the PDEA8 pre-mRNA, and optionally the editing enzymes ADAR1a, ADAR1b and ADAR2, measured in the cellular RNA extract;
- d) comparing the results obtained in step b) between said cells from said IFNα treated patient with non treated control cells or with. IFNα treated cells prior obtained from the same patient at the beginning or during the IFNα treatment.

The following examples and also the figures and the legends hereinafter have been chosen to provide those skilled in the art with a complete description in order to be able to implement and use the present invention. These examples are not intended to limit the scope of what the inventor considers to be its invention, nor are they intended to show that only the experiments hereinafter were carried out.

LEGEND TO THE FIGURES

FIG. 1:
Partial sequence of intron 9 of the PDE8A gene and coordinates of the edited adenosine residues. An internal sequence (432 bp) of intron 9 (base positions 5305 to 5736) is presented. Previously described editing sites by Orlowski and collaborators (5) are in bold and their name depicted in black capital letters above the sequence (coordinates in intron 9 of the PDE8A gene: H=5468; A=5505; B=5506; C=5536; D=5538; E=5539; F=5548; G=5617).

FIG. 2:
Overall putative stem and loop structure of RNA sequence of intron 9 of the Human gene PDE8A (bases 5367 to 5736). The 2D RNA structure is calculated by the KineFold program (http://kinefold.curie.fr/). Editing sites described by Orlowski and collaborators are depicted in red (5).

Figure 3B:
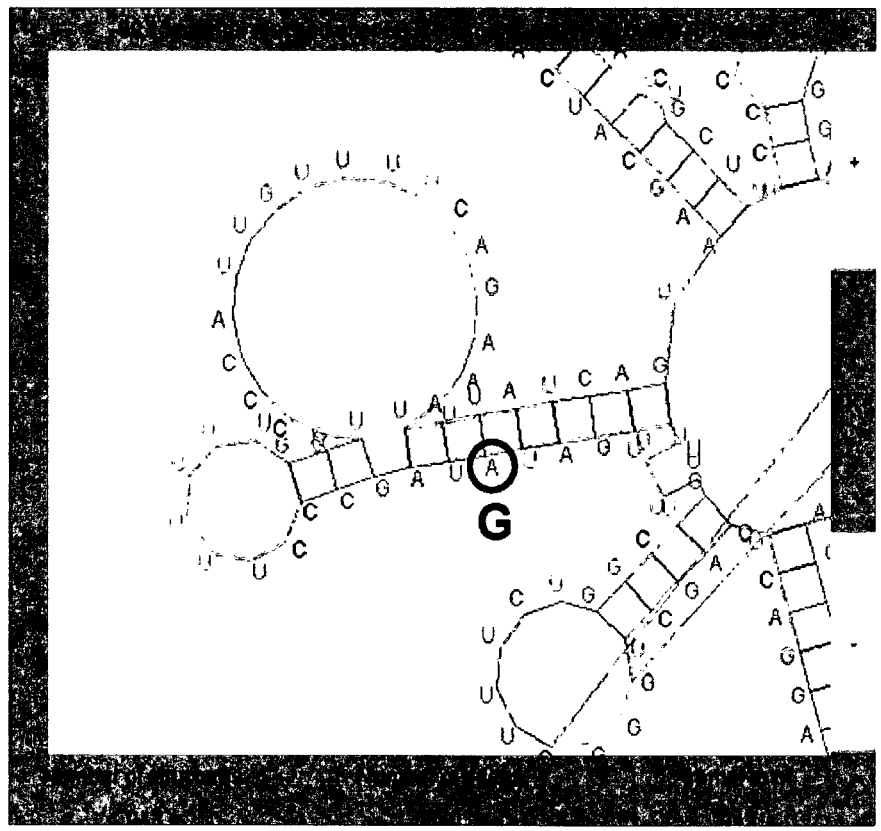

FIGS. 3A and 3B:
Zoom on editing sites A, B, C, D, E, F (3A) and G (3B). The 2D RNA structure is calculated by the KineFold program (http://kinefold.curie.fr/). Published editing sites are in black characters (5) with the exception of site H which is out of the presented 2D structure.

FIG. 4:
Edited adenosines are conserved between Human and chimpanzee. Human intronic sequence depicted in FIG. 1 (base positions 5305 to 5736) was Blasted against chimpanzee build 2.1 genome database. Alignment between the human sequence (upper raw, Query) and the Pan troglodytes reference sequence (ref|NW_001225252.1|Ptr15_WGA16816_2) (lower raw, Sbjct) is shown. Conserved adenosines are in red. Their names are in black capital letters above the aligned sequences.

FIG. 5:
Edited adenosines and intronic sequence are partially conserved between Human and Rhesus macaque. Human intronic sequence depicted in FIG. 1 (base positions 5305 to 5736) was Blasted against Rhesus monkey build 1.1 genome database. Alignment between the Human sequence (upper raw. Query) and the Macaca mulatta reference sequence ref|NW_001121189.1|Mmu7_WGA11353_1 (lower raw, Sbjct) is shown. Conserved adenosines are in red. Their names are in black capital letters above the aligned sequences.

FIG. 6:
In bold, underlined characters are presented the sequences of the Forward (FWD) and the Reverse (REV) unlabeled primers used for the first round of PCR (amplicon=495 bp). The two sequences corresponding to the FAM-labeled FWD and VIC-labeled REV primers of the second nested PCR (amplicon=175 bp) are simply underlined. The sequence corresponding to the RT primer is in italic, bold characters. The editing sites are shown with their name above the sequence. New editing sites are in capital letters. It must be noticed that with this set of primers, the H and I editing sites can't be analyzed by CE-SSCP (see FIG. 12).

FIG. 7:
Example of the limit of total RNA initial quantity necessary to obtain a constant evaluation of edited isoforms (Here the isoform B. Note that the editing profile presents an isoform B proportion independent of the degree of dilution of the total RNA quantity used for the initial RT until the smallest tested (62.5 ng).

Figure 8A:
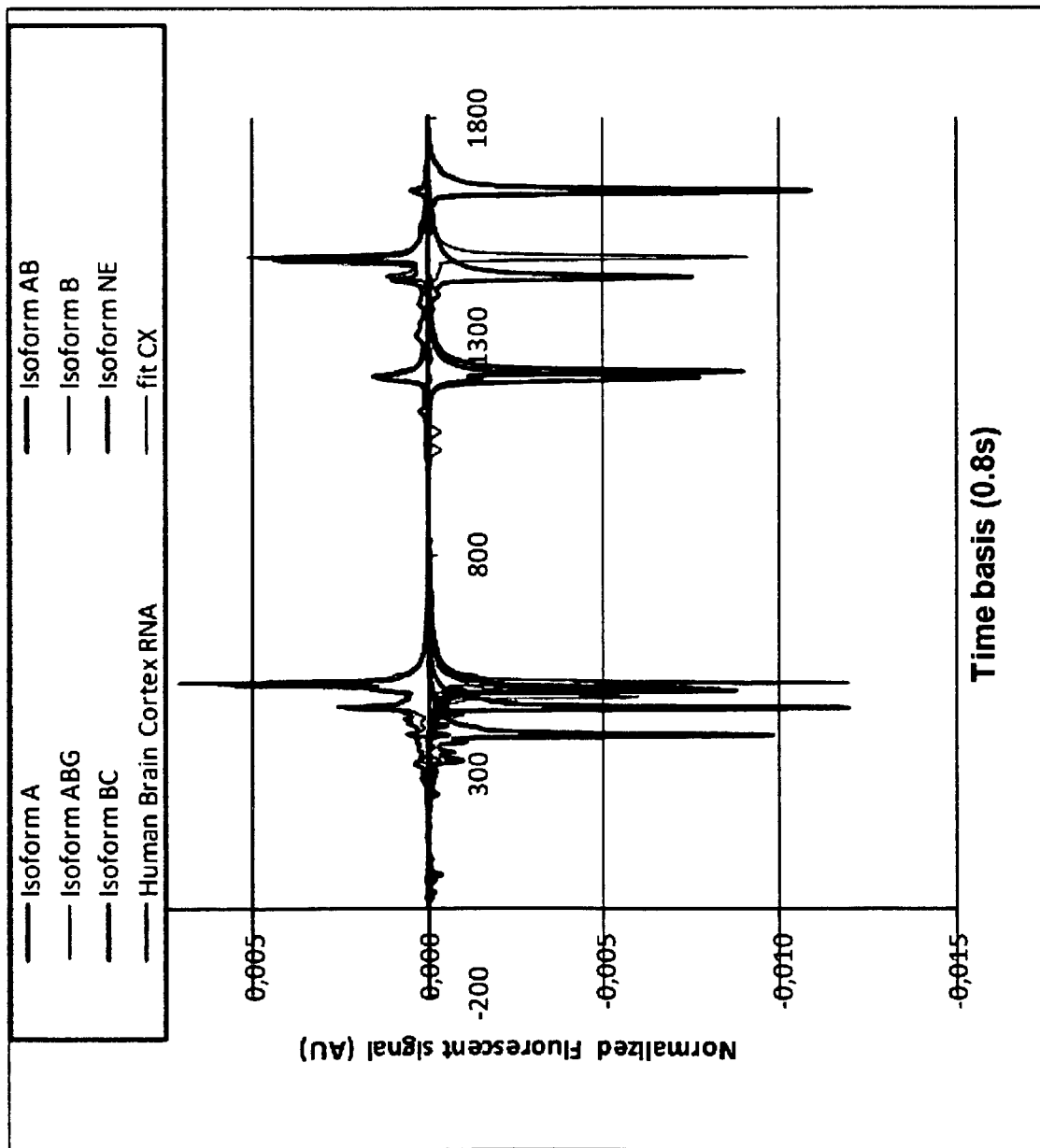
Figure 8B:
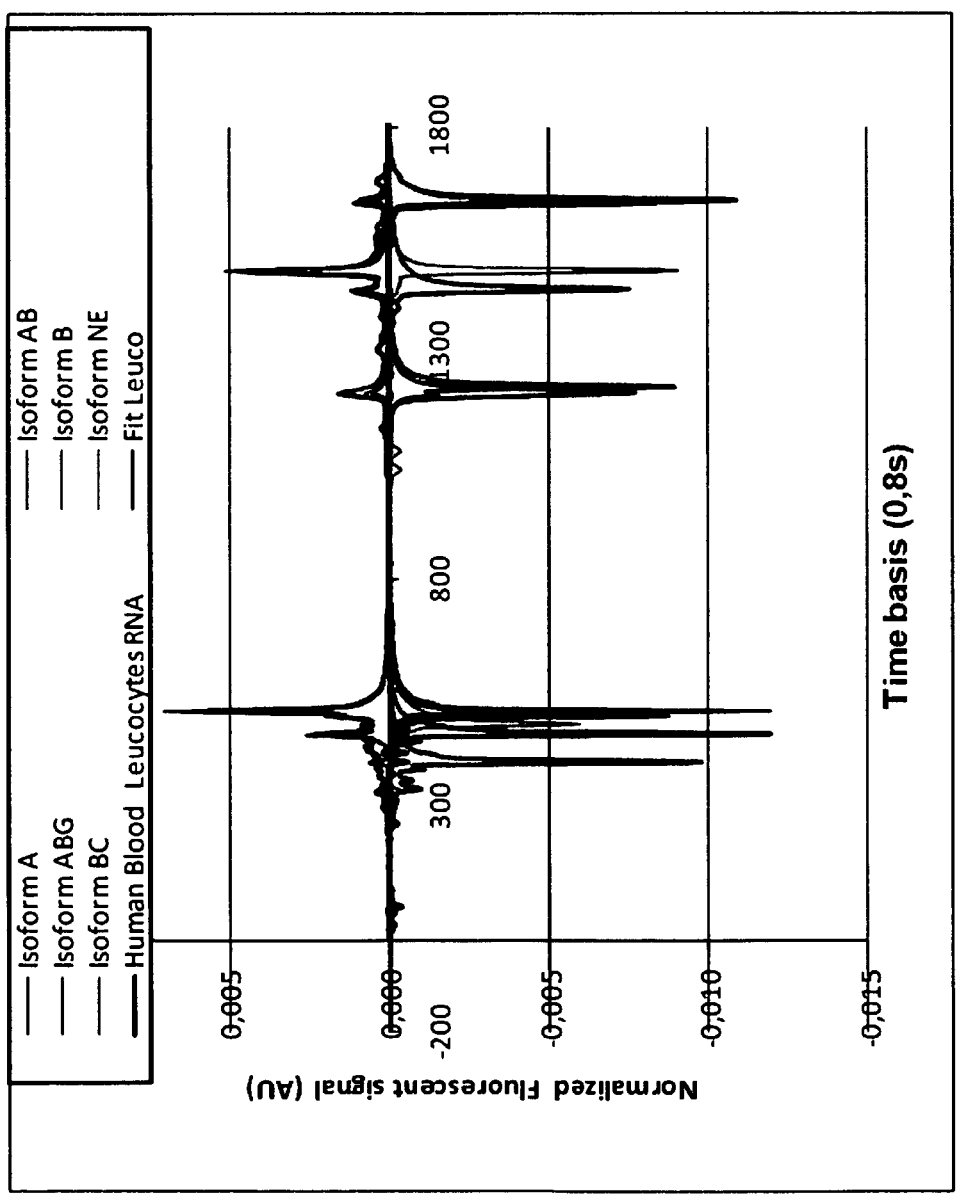
Figure 8C:
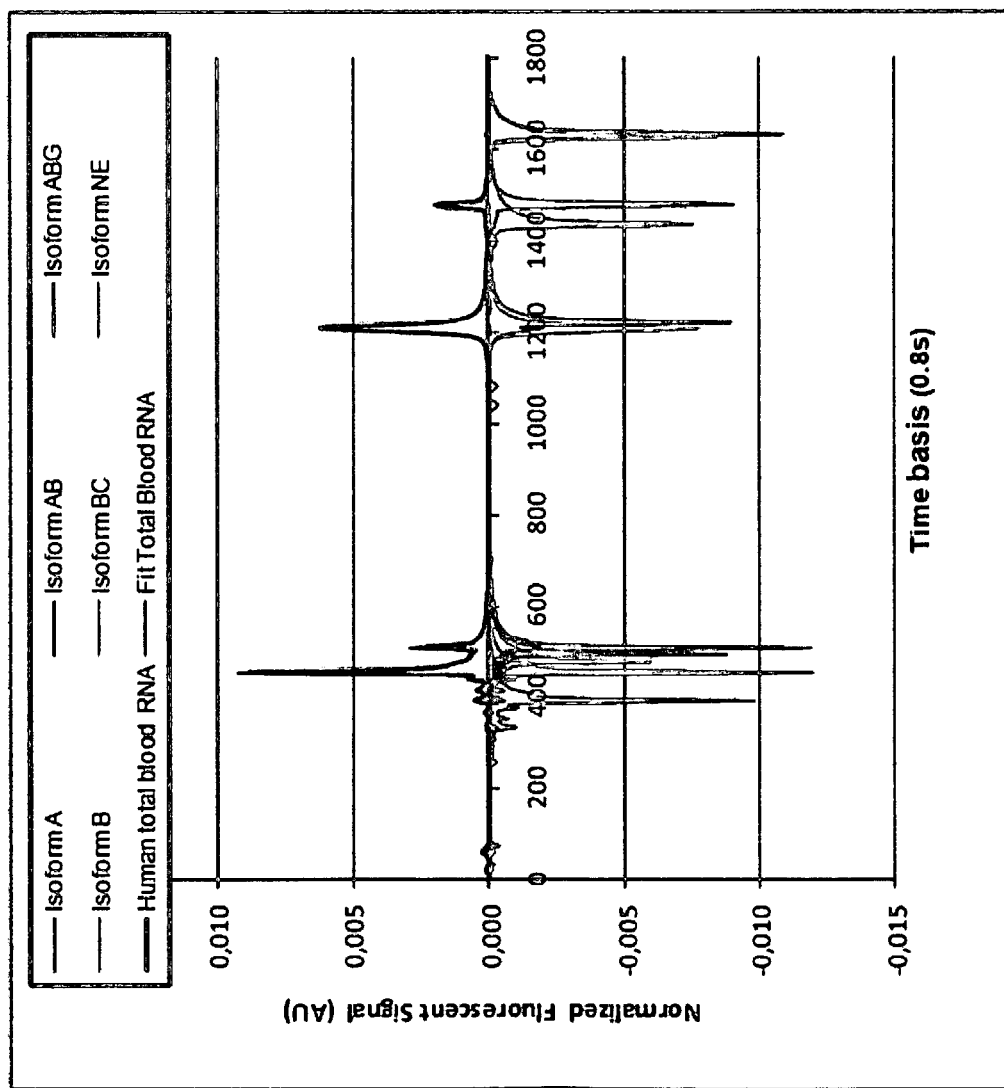

FIGS. 8A-8C:
Examples of editing profiles determined by CE from total RNA extract of different Human tissues. On the left are presented the typical analytical signals including FAM and V1C labeled strands (See material and methods). The tables indicate the respective proportions of each isoform as % of the total of the expressed edited material.

Figure 9A:
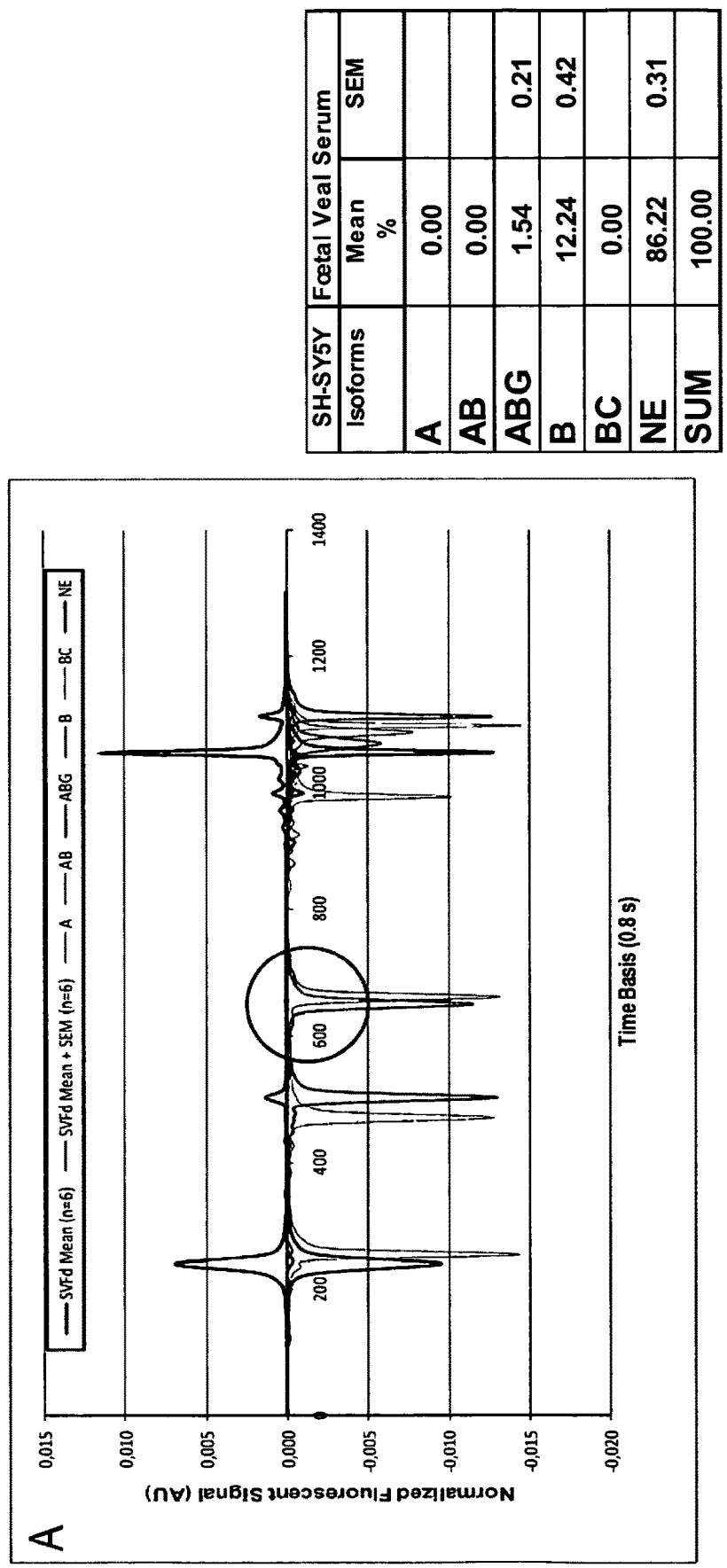
Figure 9B:
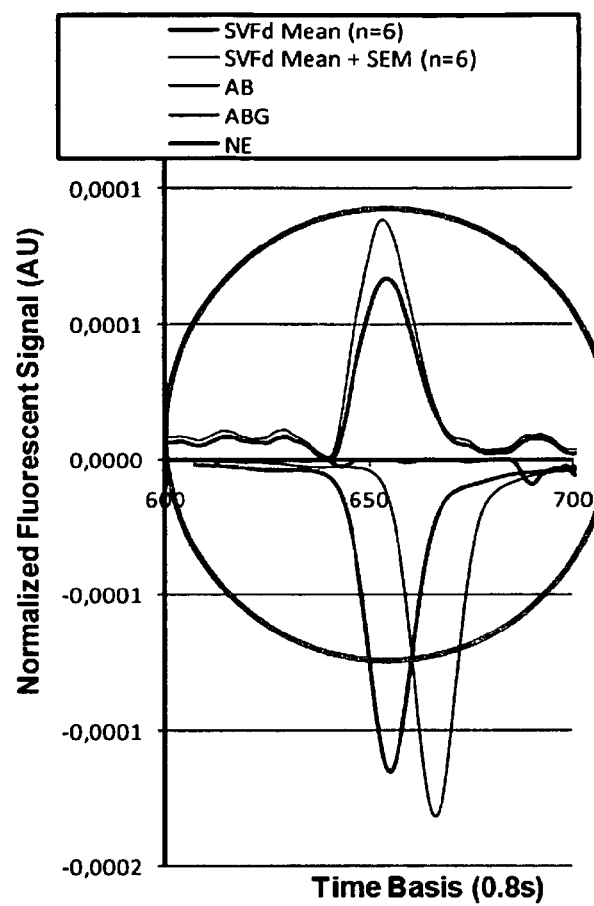

FIGS. 9A-9B:
Example of editing profile obtained from total RNA of SH-SY5 Y cells. In A the positive signals identify the mean CE signal obtained in control conditions (n=6 extracts). The negative signals correspond to Standard isoforms (See material and methods). In B the signal has been amplified between the 600 and 700 points of the time basis to give an example of the identification (here by the FAM fluorescence) of a peak which represented 1.54% of the total signal.

Figure 10:
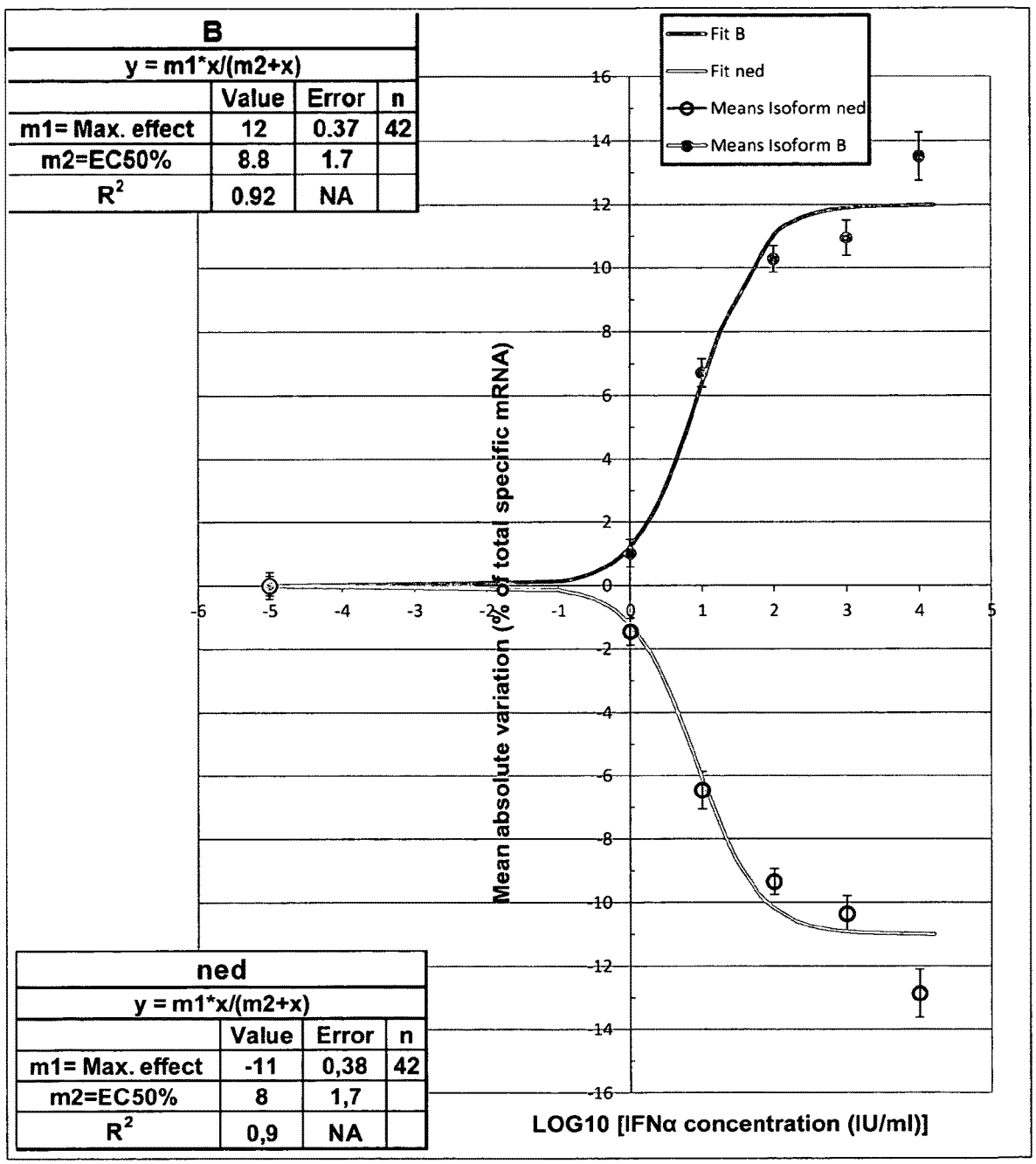

FIG. 10:
Relationship between applied IFN α concentrations and the mean Δ of variation of the B and non edited (NE) isoforms in the SH-SY5 Y cells. Each point represents the mean±SEM (n=8) of the individual values measured 48 hours after administration in the incubating medium of 0, 1, 10, 100, 1000 and 10000 IU of IFNα.

FIG. 11:
Correlation, in SH-SY5 Y cells, between the relative quantities (RQ) of ADAR1a-150 induced by increased concentrations of IFNα and the relative increase in the proportions of isoform B in the editing profile of PDE8A RNA. The isoform B is defined as the isoform in which the edited site B is alone under the edited form.

FIG. 12: Schematic representation of the edited region of the PDE8A pre-mRNA.
The edited sequence is located in intron 9 of the PDE8A gene. The sequences of the two labelled primers used for the nested PCR are shown and depicted as grey boxes in the schematic representation. Edited sites are indicated by vertical bars with their name above. Letters in italic (H and I) correspond to sites which cannot be analyzed with this set of primers.

Figures 13A, 13B:
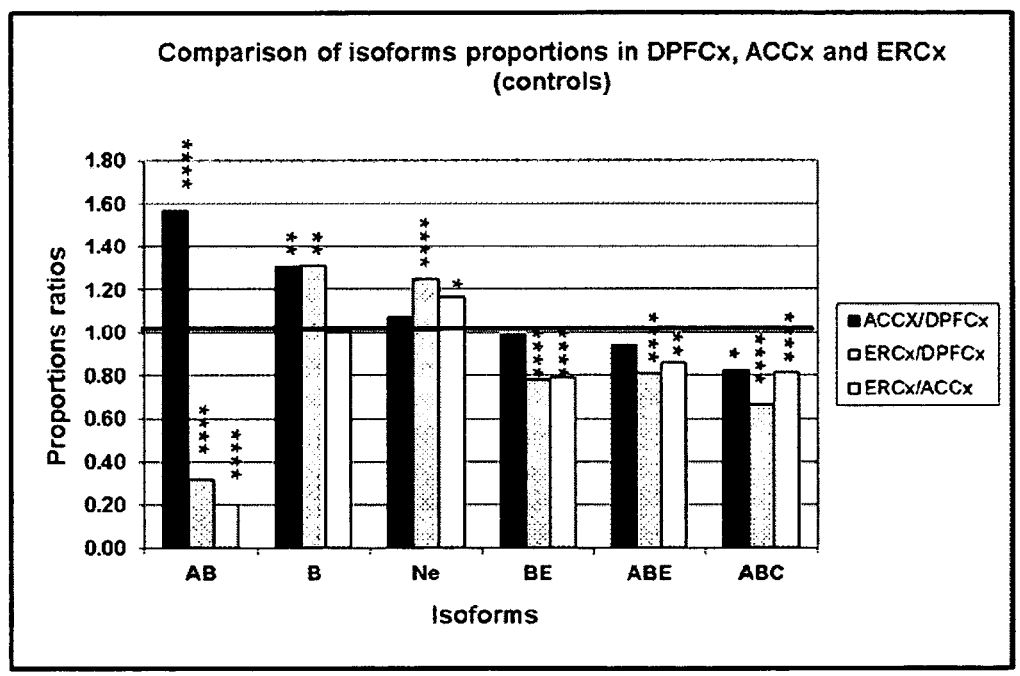

FIGS. 13A and 13B: Variations of the PDE8A pre-mRNA editing profile in three cortical areas of controls subjects. A-Proportions of PDE8A pre-mRNA editing isoforms in Dorsoprefrontal Cortex (DPFCx), Anterior Cingulate Cortex (ACCx) and Entorhinal Cortex (ERCx) of controls (n=10 for each area). Only editing isoforms with proportions higher than 3% in two over the three brain areas are presented (B, ABC, Ne, BE, ABE, AB). Standard error of the mean (SEM) are shown (n=10). B-Ratios of editing isoform proportions between DPFCx, ACCx, and ERCx in controls. Individual values were log normal (LN) transformed to provide data with a normal distribution. For each considered isoform, all possible differences between individual controls of brain areas were calculated (n=100). The mean proportions ratios between brain areas were obtained as exponential elevation of the above mentioned mean difference. For an absence of variation the ratio=1. For significance, * stands for p≤50.05,  stands for p≤0.005, * for p≤0.0005 and **** for p≤0.00005.

Figures 14A, 14B:
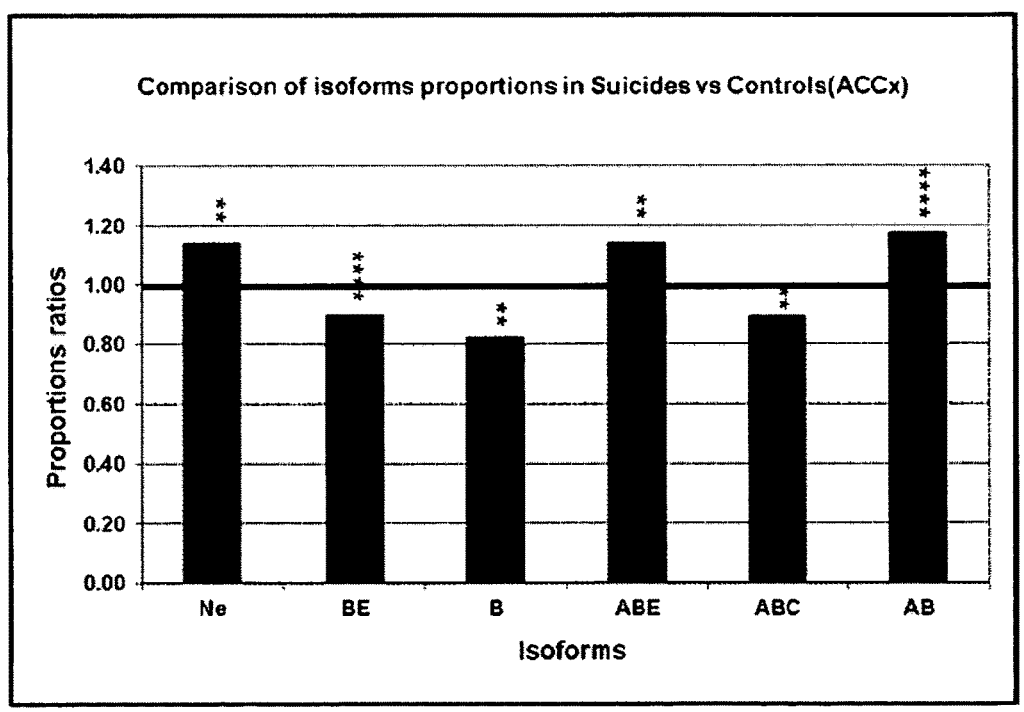

FIGS. 14A and 14B: The PDE8A pre-mRNA editing profile is significantly modified in the ACCx of depressed suicides versus controls. A-Proportions of PDE8A pre-mRNA editing isoforms in Anterior Cingulate Cortex (ACCx) of controls and depressed suicides (n=10). Editing isoforms are those considered in FIG. 13 (B, ABC, Ne, BE. ABE, AB with proportions >3%). Standard error of the mean (SEM) are shown (n=10). B-Ratios of editing isoform proportions between depressed suicides and controls in ACCx. For each considered isoform, all possible differences between LN (individual isoforms proportions) in controls of and in suicides compared to controls were calculated (n=100). The proportions ratios between suicides and controls were obtained by exponential elevation of the above mentioned mean differences. For an absence of variation the ratio=1. For significance, * stands for p≤0.05,  stands for p≤0.005, * for p≤0.0005 and **** for p≤0.00005.

Figure 15:
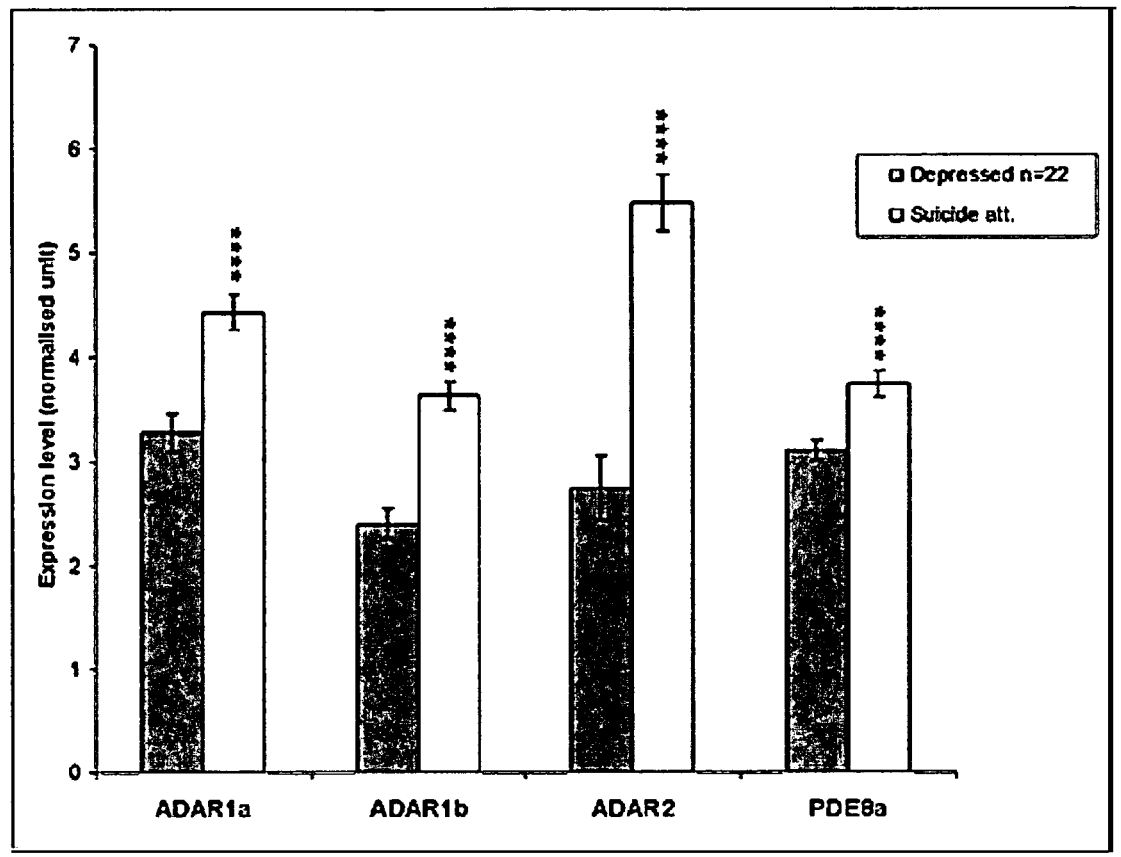

FIG. 15: mRNA expressions of ADARs and PDE8A are altered in blood samples of suicide attempters. Suicide attempters were compared to depressed patients without any suicide attempt (n=25). The ADAR1a, ADAR1b, ADAR2 and PDE8A mRNA expressions were measured from total blood (PAXgene tubes) by the Q-PCR technique with the following specific primers: HS01020780_m1; HS01017596_m1; HS00210762_m1 and HS00400174_m1 respectively (Applied Biosystems References). Results were normalized by comparison with respective values found in a reference pool of human leucocytes total RNA. [reference genes: Glyceraldehyde-3Phospate-deshydrogenase (GAPDH) and β2 microglobuline (β2M)]. For significance, **** stands for p≤0.00005.

EXAMPLES

Example I: Material and Methods

1-Cell Culture, IFNα Treatment, Cells Lysis and RNA Extraction

The SH-SY5 Y Human neuroblastoma cell line was purchased from ECACC (ref 94030304, lot number 06H021). Cells were cultured in high glucose D-MEM medium (Sigma, ref D6546) supplemented with 10% dialysed FCS (PAA, ref A15-507, lot number A50708-0050), 2 mM Glutamine (Sigma, G7513) and a IX mix of Antibiotic-Antimycotic Stabilized (Sigma, ref A5955) at 37° C. under a humidified atmosphere of 5% $CO_2$. The day preceeding hIFNα treatment, SH-SY5 Y cells were plated in 8 different 6-well plates at a density of $7.10^5$ cells/well. On the next day, culture medium was removed and cells were incubated for 48 hours with hIFNα at the correct concentration (PBL biomedical laboratories, ref 111001-1, lot number 3734). On the day of the experiment, the hIFNα stock solution ($10^5$ I·U/ml in sterile IX D-PBS stocked at −80° C.) was thawed on ice and then extemporaneously diluted in D-MEM supplemented with FCS and Antibiotic-Antimycotic, at the final concentrations of 1, 10, 100, 1000 and 1000 IU/ml. In each well, cells were treated with 2 ml of the working solution. Aliquots of the stock-solution were used only once. For controls (vehicle), cells were treated with 2 ml of supplemented D-MEM. After 48 hours of incubation, medium was discarded and cells corresponding to the 8 wells of an experimental condition were directly lysed in 600 μl of RLT lysis buffer (Qiagen, RNeasy Plus mini Kit, ref 74134) as described by furnisher.

RNA isolation and purification were carried out essentially as described by manufacturer (Qiagen, RNeasy Plus Mini kit, ref 74134). For homogenization, cell lysates were first passed through QIAshredder spin columns (Qiagen, ref 79656) placed in 2 ml collections tubes. Flow-throughs were then transferred to a gDNA Eliminator spin column of the RNeasy Plus Mini kit in order to eliminate remaining genomic DNA. RNAs were then purified on RNeasy spin columns and eluted with 40 μl of RNase-free water. Eluted RNAs were kept on ice for further experiments or stocked at −30° C. The quantity of total RNA obtained from each purification was measured with a Qubit Fluorometer (Invitrogen, ref Q32857) and the Quant-IT RNA BR assay (Invitrogen, ref Q10211). The quality of RNAs was checked by loading 1 μg of the material on a native 1.5% agarose gel. The integrity of bands corresponding to 28S and 18S rRNA was verified for each sample.

2-Isolation of PBMCs from Human Total Blood and RNA Extraction

Blood samples (2×5 ml) were collected into heparinized tubes, pooled and diluted with an equal volume of $Ca^{2+}$ and $Mg^{2+}$ free 1×PBS (Phosphate Buffer Saline) sterile solution. Two LeucoSep tubes (Greiner Bio-One, ref: 163 289 or 163 290) filled with 3 ml of pre-warmed separation medium (Ficoll-Paque Plus, GE Healthcare Bio-Sciences AB, ref: 17-1440-02) were centrifugated for 30 s at 1000 g at room temperature. Half of the diluted blood volume was carefully poured into each of the two separation medium-containing LeucoSep tubes.

After 10 minutes of centrifugation at 1000 g and room temperature, the enriched cell fractions were harvested and pooled (lymphocytes/PBMCs=white ring). The cells were then washed with 10 ml of $Ca^{2+}$ and $Mg^{2+}$ free 1×PBS sterile solution. After centrifugation 10 minutes at 250 g the dry pellet was disrupted in 1 ml of TRIzol reagent (Invitrogen). The following phase separation and RNA precipitation steps were performed according to manufacturer's instructions (TRizol Reagent, Invitrogen). The RNA pellet was washed twice with 1 ml of 75% ethanol, dried and resuspended in 50 μl of RNAse-free water. RNA concentrations were determined with a Qubit Fluorometer (Invitrogen, Q32857) and the Quant-IT RNA BR assay (Invitrogen, ref Q10211).

3-Construction of Standard Editing Isoforms for CE-SSCP Before cDNA synthesis 1 μg of total RNA (Human Blood Peripheral Leukocytes Total RNA, Clontech, ref 636580 [pool of 53 male/female Caucasians, ages: 20-50] and Human Brain Cerebral Cortex Total RNA, Clontech, ref 636561 [pool of 10 male/female Caucasians, ages: 20-68) was treated with 1 unit of RQ1 RNase-free, DNase (Promega, ref M610A) for 30 minutes at 37° C. The reaction was stopped by adding 1 μl of Stop Solution (20 mM EGTA, Promega, ref part number M199A) and then heated for 10 minutes at 65° C. for both enzyme denaturation and RNA linearization. RNA containing tubes were then immediately placed and kept on ice. DNase-treated RNAs were then reverse transcribed with the Thermoscript RT-PCR system Plus Taq (Invitrogen, ref 11146-032) and the gene specific primer PDE8A-RT:

(SEQ ID NO. 5)
5′-P-GTGGTAGGGAAAGCCAGGATG-3′OH located in intron 9 of the Human PDE8A gene. The PCR reaction (final volume 50 µl) resulting in a 202 bp fragment, was carried out on 2 µl of the reverse transcription products with 1 unit of Platinum Pfx DNA polymerase (Invitrogen, ref 11708-013) and intron 9-specific primers (forward primer:

(SEQ ID NO. 6)
5′-P-CAACCCACTTATTTCTGCCTAG-3′OH 6) and reverse primer:

(SEQ ID NO. 7)
5′-P-TTCTGAAAACAATGGGCACC-3′OH;

final concentration 0.3 µM each). After a denaturing step at 95° C. for 5 minutes, the PCR was brought to its final point after 35 cycles (30 seconds at 95° C.; 30 seconds at 62° C. with a decreasing temperature after cycle 10 by 0.5° C. every 1 cycle, and 30 seconds at 68° C.), and a final elongation step of 2 minutes at 68° C. Aliquots (5 µl) of the amplification products were used to check the quantity and the quality of amplicons on a 2% agarose analytic gel. The remaining 45 µl of each PCR reaction were run on a preparative 2% agarose gel. Under longwave UV light, agarose slices containing the PCR products were cut off and DNA was then purified with the QIAquick gel extraction kit (Qiagen, ref 28704). The purified PCR products were sent to GeneCust for cloning in the pUC57 vector, and sequencing. One hundred and fifty clones coming from both tissue sources (cerebral cortex and leukocytes) were sequenced. Sequence analysis was performed at Biocortech and the occurrence of each editing isoform quantified. Plasmids corresponding to the different editing isoforms were then amplified and used as standards in CE-SSCP experiments.

4-Reverse transcription and nested PCR

Human total blood RNA was extracted with the PAXgene Blood RNA kit 50 (PreAnalytiX, ref 762174) according to manufacturer's instructions. Total RNA was treated with RQ1 RNase-free, DNase (Promega, ref M610A) for 30 minutes at 37° C. The reaction was stopped by adding 1 µl of Stop Solution (20 mM EGTA, Promega, ref part number M199A) and then heated for 10 minutes at 65° C. for both enzyme denaturation and RNA linearization. RNA containing tubes were then immediately placed and kept on ice. One microgram, 500 ng, 250 ng, 125 ng or 62.5 ng of DNase-treated RNAs were reverse transcribed with the Thermoscript RT-PCR system Plus Taq (Invitrogen, ref 11146-032) and the gene specific primer PDE8A-RT:

(SEQ ID NO. 5)
5′-P-GTGGTAGGGAAAGCCAGGATG-3′OH located in intron 9 of the Human PDE8A gene. The first PCR reaction (final volume 25 µl) resulting in a 495 bp fragment, was carried out on 1 µl of the reverse transcription products with 1 unit of Platinum Taq DNA polymerase (Invitrogen, ref 11146-032) and intron 9-specific unlabeled primers (forward primer:

(SEQ ID NO. 8)
5′-P-GCTGAAGCCTTCCTTCTAAGG-3′OH and reverse primer:

(SEQ ID NO. 9)
5′-P-CCTGGGTCAACTCTAGGTCC-3′OH;

final concentration 0.3 µM each). After a denaturing step at 95° C. for 3 minutes, the PCR was brought to its final point after 35 cycles (30 seconds at 95° C., 30 seconds at 50° C., and 30 seconds at 72° C.), and a final elongation step of 2 minutes at 72° C. Products of this first PCR were checked on a 2% agarose analytic gel and then diluted 1:100 for the second round PCR. This second reaction (final volume 25 µl) resulting in a 175 bp fragment, was carried out on 1 µl of the 1:100 dilutions with 1 unit of Platinum Pfx DNA polymerase (Invitrogen, ref 11708-013) and intron 9-specific labeled primers (forward primer:

(SEQ ID NO. 10)
FAM-5′-P-CTAGGGAACCCTGTTTAGTCC-3′OH and reverse primer:

(SEQ ID NO. 11)
VIC-5′-P-CAATGGGCACCAAAAAAGGG-3′OH;

final concentration 0.3 µM each). After a denaturing step at 94° C. for 4 minutes, the PCR was brought to its final point after 35 cycles (30 seconds at 95° C. 30 seconds at 50° C., and 30 seconds at 68° C.), and a final elongation step of 2 minutes at 68° C. Aliquots (5 µl) of the amplification products were used to check the quantity and the quality of amplicons on a 2% agarose analytic gel.

For other RNA sources (Total RNA from T-Helper/Inducer Lymphocytes (CD4-positive), Yorkshire Bioscience, ref N1121; Human Blood Peripheral Leukocytes Total RNA, Clontech, ref 636580; Human Brain Cerebral Cortex Total RNA. Clontech, ref 636561 and total RNA from PBMC or SH-SY5 Y Neuroblastoma cell line), 500 ng of total RNA were reverse transcribed and the resulting cDNAs amplified by nested-PCR as described above.

5-Quantilication of ADAR1a-p150 mRNA Expression by Real-Time PCR Analysis

In order to quantify levels of ADAR1a mRNA expression in SH-SY5 Y cells first-strand cDNA was synthesized by reverse transcription (as described above) and subjected to TaqMan quantitative Real-Time PCR analysis (Applied Biosystems). The probe and primers used for the quantitative PCRs were from Applied Biosystems (Gene Expression Assays, Assay-On-Demand):

ADAR1a: ref Hs 01020780_ml

Human GAPDH (product no. 4326317E; Applied Biosystems) was included in each multiplex PCR as an internal control. Q-PCR and subsequent analysis were performed with a 96-well block StepOnePlus real-time PCR system (Applied Biosystems).

Quantitation of target gene expression in all samples was normalized to GAPDH expression by the equation Ct (target)−Ct (GAPDH)=ΔCt, where Ct is the threshold cycle number. The mean ΔCt value of samples from untreated cells was determined and used as a reference point for the samples corresponding to IFNα treated cells. Differences between untreated and treated cells, including individual variation were calculated by the equation ΔCt (individual treated samples)−ΔCt (mean of untreated samples)=ααCt. Changes in target gene expression (n-fold) in each sample were calculated by $2^{-\Delta\Delta Ct}$, from which the means and standard deviations (SD) were derived.

6-Separation of Single-Strand cDNA Fragments by Capillary Electrophoresis (CE-SSCP).

For the analysis of FAM- and VIC-labelled cDNA fragments by mean of their unique single-strand conformational polymorphism (SSCP), the fluorescent PCR products (1 µl of a 1:20 to 1:200 dilution) plus deionized formamide (11 µl) were added to a mixture of migration and editing isoform standards (0.5 µl). The migration standards are PCR amplicons of different sizes labeled with the ROX fluorescent dye (Eurofins MWG operons). They are used for the calibration of the electrophoresis migration in capillaries. Editing isoform standards (both FAM- and VIC-labelled)—whose construction has been described above-are used for unambiguous identification of the different editing isoforms present in the different samples. Before loading, the mixtures of samples and standards were denatured for 2 minutes at 90° C. and then immediately chilled on ice. Non-denaturing electrophoresis was carried out in an ABI PRISM® 3100-Avant Genetic Analyzer (Applied Biosystems) through 80 cm-long capillaries filled with 7% "POP™ Conformational Analysis Polymer" (Applied Biosystems), 1× Tris-borate-EDTA and without glycerol. After a pre-run carried out at 15 kV for 3 min, samples were injected for 15 s at 2 kV, and electrophoresis was performed for 105 min at 15 kV, at a strictly controlled temperature of 24° C. In these conditions, an individual retention time was obtained for each editing isoform. The procedures used for CE-SSCP analysis of RNA editing has been extensively described in the article by Poyau and collaborators (16).

7-Identification and Relative Quantization of Each cDNA Form in a Complex Mixture.

Raw data obtained from the ABI PRISM® 3130xlt Genetic Analyzer were extracted for signal processing by the Peak-Fit® (v 4.11) software. After base-line treatment and normalization of each electrophoresis profile (FAM- or VIC-labeled fragments) the relative abundance of the different edited isoforms was quantified thanks to an in-house software allowing deconvolution of the isoform and sample signals in an unique time basis.

8-Proteins Extractions and Western-Blot Analysis

After culture medium elimination, SH-SY5 Y cells were washed two times with a phosphate buffer solution (PBS, Gibco Invitrogen Corporation), scraped and solubilized for 2 hr at 4° C. in solubilization buffer containing 150 mM NaCl, 5 mM EDTA, 1% Triton X-100, 0.1% sodium deoxycholate, 10 mM Tris-HCl [pH 8.0] and supplemented with protease inhibitors (1 mM phenylmethylsulfonyl fluoride, and one tablet of Complete™ mini protease inhibitors cocktail [Roche]). The lysate was then centrifugated for 10 min at 13.000×g at 4° C. to pellet cell debris. Proteins present in the supernatant (clear lysate) were quantified with a Qubit Fluorometer (Invitrogen, Q32857) and the Quant-IT Protein assay (Invitrogen, ref Q33211).

75 µg of the clear lysates corresponding to each experimental condition were resolved on 4-20% Tris-HCl gel (Bio-Rad, Criterion Precast Gels ref 345-0033) at 100V for 3 hours.

Proteins (clear lysates from whole cell extracts) were then transferred onto nitrocellulose membrane (nitrocellulose transfer membrane Protran BA 85, Schleicher and Schuell) using Towbin buffer (Towbin et al., 1979. PNAS, 76, 4350-4354) and a semi-dry electrotransfer device (Bio-Rad). After transfer, membranes were blocked, in 5% non-fat dried milk in TBST (10 mM Tris-HCl [pH 8.0], 150 mM NaCl, 0.05% Tween 20) supplemented with sodium azide (0.1%) for 2 hr. The membrane was then incubated for 16 hr at room temperature with the primary antibody (Santa-Cruz, anti-PDE8A (C-15) ref sc-17232) diluted 1:200 in the same buffer. After several washes with TBST, the blot was incubated with a Alexa Fluor 680 anti-goat secondary antibody (Invitrogen, A21088) diluted 1:10000. Signal was then read on an Odyssey machine (LiCor Biosciences).

9-CE-SSCP Method, Particularly for the Determination of the Editing Profile of the 5-HT2C Receptor The method used for CE-SSCP determinations was already described for human samples (see patent PCT/EP 2008/057519 filed on Jun. 13, 2008 and patent PCT/EP2009/067464 filed on Dec. 17, 2009).

Example II: The A to I Editing of PDE8A is Specific of More Evolved Primates Including Man Interestingly, as shown in FIG. 4 all the adenosines described as edited in intron 9 of the PDE8A Human gene (A, B, C, D, E, F, and G) are conserved in the corresponding intronic sequence of chimpanzee. The overall identity is very high=428/432 (99%), and there is no gaps=0/432 (0%) in the two sequences alignment. This very high similarity of sequences, and potentially of secondary structures, between the two introns strongly suggest that the adenosines residues could be edited in chimpanzee as they are in Human sequence.

In the Rhesus monkey sequence the adenosines are partially conserved, see FIG. 5. Actually, the A site of editing is not present in the Rhesus sequence and the overall sequence homology is lower than the one observed with chimpanzee=399/433 (92%). Moreover 10 gaps/433 (2%) are detected implying a lower conservation of the 2D RNA structure. Similar BLAST analysis against mouse and rat genomes show that the sequence of intron 9 of gene PDE84 is not conserved in these two other species. These results suggest that the potential editing of intronic sequence (intron 9) of gene PDE8A is limited to primates in mammals. The functional reasons for this editing conservation are unknown but may imply higher cerebral activities in primates and notably mood disturbances. Finally the possible editing of sites in intron 9 of the PDE34 gene appears specific to some primate species with 8 already identified sites conserved in Human and Chimpanzee.

Example III: The Identification of the Editing Sites in this Genomic Region has been Completed by Cloning and Sequencing Technique Realized on 150 Clones from Both Human Brain Cerebral Cortex and Leukocytes RNA Extracts (see Example 1: materials and methods)

These new edited sites are named: 1, J, K, L, M, N, and the corresponding expressed edited isoforms are presented on the following table:

Table 1: New editing sites and corresponding edited isoforms in different human tissues.

TABLE 1

New editing sites coordinates (underlined in bold)

| Editing sites | Coordinates in intron 9 of PDE8A gene |
|---|---|
| A | 5505 |
| B | 5506 |
| C | 5536 |
| D | 5538 |
| E | 5539 |
| F | 5548 |
| G | 5617 |
| H | 5468 |
| I | 5482 |
| J | 5500 |
| K | 5503 |
| L | 5544 |
| M | 5572 |
| N | 5590 |

TABLE 2

Editing isoforms observed in Human leukocytes (150 clones sequenced). Editing isoforms >1% are in bold characters.

| Isoforms | Number of clones | %/Total | |
|---|---|---|---|
| A | 0 | 0,0 | 1 |
| AB | 2 | 1,3 | 1 |
| ABDF | 1 | 0,7 | 2 |
| ABE | 1 | 0,7 | 2 |
| ABG | 1 | 0,7 | 1 |
| ABK | 1 | 0,7 | 3 |
| B | 68 | 45,3 | 1 |
| BC | 10 | 6,7 | 1 |
| BCD | 2 | 1,3 | 2 |
| BCE | 2 | 1,3 | 2 |
| BCF | 2 | 1,3 | 2 |
| BCG | 1 | 0,7 | 2 |
| BD | 10 | 6,7 | 2 |
| BDE | 2 | 1,3 | 2 |
| BDL | 1 | 0,7 | 3 |
| BE | 4 | 2,7 | 2 |
| BEF | 2 | 1,3 | 2 |
| BF | 2 | 1,3 | 2 |
| BFG | 1 | 0,7 | 2 |
| BG | 3 | 2,0 | 2 |
| BH | 1 | 0,7 | 2 |
| BK | 1 | 0,7 | 3 |
| D | 1 | 0,7 | 2 |
| FGM | 1 | 0,7 | 3 |
| *ned | 30 | 20,0 | 1 |

*ned: Non Edited isoform
1 Editing isoforms already identified in PBMC
2 Editing isoforms identified in a pool of leukocytes
3 Isoforms with new editing sites

TABLE 3

Editing Isoforms observed in Human brain cerebral cortex (150 clones sequenced). Editing isoforms >1% are in bold characters.

| Isoforms | Number of clones | %/Total | |
|---|---|---|---|
| A | 0 | 0,0 | 1 |
| AB | 11 | 7,3 | 1 |
| ABC | 5 | 3,3 | 2 |
| ABCDEFG | 1 | 0,7 | 2 |
| ABCEF | 1 | 0,7 | 2 |
| ABCG | 1 | 0,7 | 2 |
| ABDE | 1 | 0,7 | 2 |
| ABDEFG | 1 | 0,7 | 2 |
| ABDEG | 1 | 0,7 | 2 |
| ABE | 2 | 1,3 | 2 |
| ABEF | 2 | 1,3 | 2 |
| ABEFG | 3 | 2,0 | 2 |
| ABEG | 1 | 0,7 | 2 |
| ABF | 1 | 0,7 | 2 |
| ABFG | 1 | 0,7 | 2 |
| ABFGI | 1 | 0,7 | 3 |
| ABG | 2 | 1,3 | 2 |
| ABN | 1 | 0,7 | 3 |
| B | 64 | 42,7 | 1 |
| BC | 9 | 6,0 | 1 |
| BCDEFG | 1 | 0,7 | 2 |
| BCEG | 1 | 0,7 | 2 |
| BCFG | 1 | 0,7 | 2 |
| BCG | 1 | 0,7 | 2 |
| BD | 3 | 2,0 | 2 |
| BE | 4 | 2,7 | 2 |
| BEG | 5 | 3,3 | 2 |
| BF | 3 | 2,0 | 2 |
| BFG | 2 | 1,3 | 2 |
| BG | 4 | 2,7 | 2 |
| BH | 1 | 0,7 | 2 |
| BJ | 1 | 0,7 | 3 |
| M | 2 | 1,3 | 3 |
| ned* | 12 | 8,0 | 1 |

*ned: Non Edited isoform
1 Editing isoforms already identified in PBMC
2 Editing isoforms identified in a pool of cortex
3 Isoforms with new editing sites An additional interest of this discovery was to allow the preparation of standards of each expressed edited isoforms in the brain and peripheral human tissues and in human derived cell lines. It was realized by subcloning RT-PCR products in the pUC57 vector as indicated in method section.

Example IV: The Conditions of the Precise Measurement of the Distribution of the Edited and Non Edited Isoforms of the PDE8A Pre-mRNA were then Validated and Presented Here in Different Tissues or Cells as an Example Thus, in Human tissues, the identification of these 14 editing sites could conduct to a theoretical combination of $2^{14}$ pre-RNA isoforms and it was important to establish the degree of complexity of the editing profile in different human tissues and human cell lines.

As typical examples the editing profile of PDE8A was identified and its quantification validated in Human brain cerebral cortex RNA, in human Peripheral Blood Mononuclear Cell (PBMC) total RNA, in Total blood RNA and in SH-SY5 Y human cell line (Neuroblastoma derived) (see figures). In these cells the effect of interferon alpha, (a molecule known to induce severe mood adverse effects in 20 to 50% treated patients (14,15) was evaluated and allowed to demonstrate the interest of editing profiling to follow the alterations of the activity of editing enzymes. Starting from a total RNA extract the conditions of amplification of the gene sequence including the 7 edited sites were tested to allows a limit of initial total RNA quantity below 70 ng, and to obtained the best combination of forward and reverse specifically labeled single strands allowing specific separation of expressed isoforms by capillary electrophoresis. Finally, to obtain the best sensitivity (adequate results for 62 ng of starting RNA material for RT) and adequate identification of expressed isoforms the following two steps nested PCR was validated using the following primers:

Thus, the defined primers are:
1st PCR/unlabeled primers:

PDE8A-1REV
(SEQ ID NO. 12)
GGACCTAGAGTTGACCCAGG

PDE8A-1FWD
(SEQ ID NO. 13)
GCTGAAGCCTTCCTTCTAAGG

2d PCR/FAM FWD labeled and VIC REV labeled primers:

PDE8A-2Rev VIC
(SEQ ID NO. 11)
CAATGGGCACCAAAAAGGG

PDE8A-2FowFAM
(SEQ ID NO. 10)
CTAGGGAACCCTGTTTAGTCC

This choice was the result tom a specific screening in order to determine the best sensitivity (limit of use of initial concentrations of total RNA in a given sample) and the best reliability of the PCRs products and the best length of the single strand to allows a good separation of the majority of the expressed isoforms in a given tissue (see FIGS. 7, 8A-8C and 9A-9B).

TABLE 4

| SH-SY5Y | Fœtal Veal Serum | |
| --- | --- | --- |
| Isoforms | Mean % | SEM |
| A | 0.00 | |
| AB | 0.00 | |
| ABG | 1.54 | 0.21 |
| B | 12.24 | 0.42 |
| BC | 0.00 | |
| ned | 86.22 | 0.31 |
| SUM | 100.00 | |

*ned: Non Edited isoform

Example V: Identification of the Editing Isoforms Profile as a Reliable Index of the Alterations of the Activities of the Editing Enzymes As an example the alteration produced by the pharmacological modulation of the expression of the ADAR1a-150 isoenzyme was tested on SH-SY5 Y cell line. The results are summarized in FIG. 10.

Thus is demonstrated that, in this cell line, the positive variation of the Isoform B expression is clearly concentration dependable. The ned isoform symmetrically negatively decrease in proportion indicating that the isoform B is mainly if not exclusively produced by the ADAR1a-p150 since its variation closely correlates with the variation of expression of this editing enzyme (See FIG. 11). The EC 50% which was calculated from this study was in the same order of value than the EC50% already demonstrated for the editing of the 5-HT2cR in the same conditions in the same cell line.

Example VI: PDE8A is Expressed in the Brain and an Editing Profile can be Observed The PDE8A RNA edited isoforms characterized by their edited sites can thus be identified from total brain RNA following a process which can be summarized as follows:

Material and Methods

Brains were collected at autopsy, sectioned coronally, flash-frozen and stored at −80° C. until dissection. Cerebral trauma, central nervous system pathology, alcoholism or drug use disorder were exclusion criteria. Brain samples were assayed and analyzed by personal blinded to the cause of death. pH was measured in the cerebellum. A psychological autopsy was used to obtain DSM-IV Axis I and II diagnoses.

Control subjects (n=10) died from causes other than suicide and did not meet criteria for any Axis I during their lifetime. Suicides (n=10) met criteria of the Columbia classification of suicidal behavior.

Brains Regions and RNA Extraction

The dorsolateral prefrontal (Brodmann area 9, DPFCx), anterior cingulate (Brodmann area 24, ACCx) and entorhinal (Brodmann area 28/34, ERCx) cortex were selected as regions of interest because they have been consistently implicated as being altered in depression and/or suicide. Wet weight of tissue (mean±SEM) was 80±4 mg in DPFCx, 84±4 mg in ACCx and 80±5 mg in ERCx.

Total RNA was isolated from affinity columns using RNeasy lipid Tissue Mini Kit (Qiagen). Genomic DNA contamination was removed by on-column DNase digestion. The yield of total RNA (absorbance at 260 nm) ranged from 12 to 57 µg. The total amount of RNA used for the reverse transcription of each sample was uniformly 1 µg.

Reverse Transcription, Nested-PCR and Identification and Relative Quantification of Each Brain Sample As described in previous sections of material and methods.

Statistical Analysis

Individual values were log normal (LN) transformed to provide data with a normal distribution. Each expressed isoform, each cortical investigated brain region, each group of subjects was then precisely indexed and were used as independent variables. The all possible differences between individual LN transformed proportions of the isoforms measured in controls individuals in the 3 regions (DPFCx, ACCx and ERCx) or in suicides and controls individuals in one particular region (the ACCx in this example) were analysed by discriminant ANOVA and adequate post hoc analysis (Scheffé test).

The p values are given for no differences between regions or subjects groups and the differences are considered as significant for $p \leq 0.05$.

Results

The Editing Profile of the PDE8A Pre-mRNA is Significantly Different in the Three Cortical Regions (FIGS. 13 A and B) and Altered in Depressed Suicides Versus Controls (FIG. 14 as an Example)

First, we have established the editing profile of the PDE8A pre-mRNA in three brain areas of the controls subjects [Dorsolateral Prefrontal Cortex (DPFCx), Anterior Cingulate Cortex (ACCx) and Entorhinal Cortex (ERCx)]. Six editing isoforms with proportions higher than 3% in at least one of the three brain areas (B, ABC. Ne, BE, ABE, AB) were analyzed (see FIG. 13A). For each of these isoforms, the ratios of their proportions in the DPFCx, the ACCx and the ERCx are presented in FIG. 13B. Significant variations were observed between the different areas and notably in the case of the AB isoform which is differentially expressed in the three cortical areas (compare DPFCx vs ERCx, and ACCx vs ERCx). These results evidenced the fine regulation of the PDE8A pre-mRNA editing in the brain of controls subjects depending on the identity and functional steady state of the cell networks which are using PDE8A as a metabotropic regulator.

In a second step the proportions of the same isoforms were compared between controls subjects and depressed suicides in the three cortical areas. As an example the proportions of the six isoforms in the ACCx of depressed suicides versus controls is presented in FIG. 14A. For each of the six isoforms, the ratios of their proportions in depressed suicides versus controls is shown in FIG. 14B. The editing profile of the PDE8A pre-mRNA is significantly modified in the ACCx of depressed suicides with editing isoforms up and down regulated likely in different cell compartments.

Example VI: mRNA Expressions of ADARs and PDE8A are Altered in Blood Samples of Suicide Attempters PDE8A is present in total blood like the editing enzymes. It was thus interesting to approach the possible alteration of the expression of editing enzymes and of the PDE8A mRNA to see if this target of the RNA editing was altered as a result of a particular suicide risk. An example of the alteration of both editing enzymes ADAR1a, ADAR1b and ADAR2 and of one of their target PDE8A expression has been demonstrated by measuring these markers in two populations of patients. The first one was depressed subjects tested just after a suicide attempt (considered as a particular suicide risk population (SuicideAtt), the second one used as control was included as depressed (MD) without any suicide attempt. The initial result is summarized on FIG. 15, obtained after determination of the steady state of these biomarkers RNA concentrations in total blood.
Example of Alteration of PDE8A mRNA Expression Associated with Suicidality in Blood of Suicide Attempters
The alteration of levels of expression of editing enzymes and PDE8A was observed in suicide attempters compared to depressed patients without any suicide attempt (n=25). ADAR1a, ADAR1b ADAR2 and PDE8A mRNA were measured from total blood (sampled in PAXgene RNA tubes). ADAR1a, ADAR1b, ADAR2 and PDE8A mRNA steady state concentrations were measured by QPCR from 500 ng of total RNA samples by using specific primers (HS01020780_ml; HS01017596_ml; HS00210762_ml and HS00400174_m1 respectively, Applied Biosystems references) and normalized by comparison with respective values found in a reference pool of human leucocytes total RNA. [reference genes: Glyceraldehyde-3Phospate-deshydrogenase (GAPDH) and β2 microglobuline (β2M)]. We note the highly significant alteration of editing occurring in suicide attempters.
Finally Brain PDE8A pre-mRNA editing profile is modified in suicides victims. On the other hand, editing enzymes and PDE8A expressions are altered in the blood of suicide attempters. This particular regulatory capacity which is unique in Man and pre-Human primates represents a particularly interesting way to evaluate by blood testing suicide risk.
This example illustrates the strong alteration of the editing process in relation with the suicide risk. The PDE8A is concerned as well as the editing enzymes and it can be suggested that the editing of a non coding sequence of this target could be directly or indirectly involved in the regulation of the expression of this target.

REFERENCES

1—Jin Billy Li, Erez Y. Levanon, Jung-Ki Yoon, John Aach, Bin Xie, Emilie LePrmust, Kun Zhang, Yuan Gao, George M. Church: Genome-Wide Identification of Human RNA Editing Sites by DNA Parallel DNA capturing and Sequencing. Science 2009, 324: 1210-1213.
2—Tim D. Werry, Richard Loiacono, Patrick M. Sexton, Arthur Christopoulos: RNA editing of the serotonin 5-HT2c receptor and its effects on cell signaling, pharmacology and brain function. Pharmacol. Ther. 2008, 119: 7-23.
3—Peter H. Seeburg, Miyoko Higuchi, Rolf Sprengel: RNA editing of brain glutamate receptor channels: mechanism and physiology. Brain Res. Reviews 1998, 26: 217-229.
4—Daniel P. Morse, P. Joseph Aruscavage, and Brenda L. Bass: RNA hairpins in noncoding regions of human brain and Caenorhabditis elegans-mRNA are edited by adenosine deaminases that act on RNAs. Proc. Natl. Acad. Sci. USA 2002, 99: 7906-7911.
5—Robert J. Orlowski, Kenneth S. O'Rourke, Irene Olorenshaw, Gregory A. Hawkins, Stefan Maas and Dama Laxminarayana: Altered editing in cyclic nucleotide phosphodiesterase 8A1 gene transcripts of systemic lupus erythematosus T lymphocytes. Immunology 2008, 125: 408-419.
6—M. Ohman: A-to-I editing challenger or ally to the microRNA process. Biochimie 2007, 89: 1171-1176.
7—S Dracheva, N Patel, D A Woo, S M Marcus, L J Siever, and V Haroutunian: Increased serotonin 2C receptor mRNA editing: a possible risk factor for suicide. Mol. Psychiatry 2008, 13: 1001-1010.
8—Peter Holmans, George S. Zubenko, Raymond R. Crowe. J. Raymond DePaulo Jr., William A. Scheftner, Myrna M. Weissman. Wendy N. Zubenko, Sandra Boutelle, Kathleen Murphy-Eberenz, Dean McKinnon. Melvin G. McInnis, Diana H. Marta, Philip Adams, James A. Knowles, Madeleine Gladis, Jo Thomas, Jenifer Chellis, Erin B. Miller, and Douglas F. Livinson: Genomewide Significant Linkage to Recurrent, Early-Onset major Depressive Disorder on Chromosome 15q. Am. J. Hum. Genet. 2004, 74: 1154-1167.
9—Peter Holmans, Myrna M. Weissman, George S. Zubenko, William A. Scheftner, Raymond R. Crowe, J. Raymond DePaulo Jr., James A. Knowles, Wendy N. Zubenko, Kathleen Murphy-Eberenz, Diana H. Marta, Sandra Boutelle, Melvin G. McInnis, Philip Adams. Madeleine Gladis, Jo Steele, Erin B. Miller, James B. Potash, Dean F. McKinnon, and Douglas F. Livinson: Genetic of Recurrent Early-Onset Major Depression (GenRED): Final Scan Report. Am. J. Psychiatry. 2007, 164: 248-258.
10—Peter McGuffin, Jo Knight. Gerome Breen, Shyama Brewster, Peter R. Boyd, Nick Craddock, Mike Gill, Ania Korszun, Wolfgang Maier, Lefkos Middleton, Ole Mors, Michael J. Owen, Julia Perry, Martin Preisig, Theodore Reich, John Rice, Marcella Rietschel, Lisa Jones, Pak Sham, and Anne E. Farmer: Whole genome linkage scan of recurrent depressive disorder from the depression network study. Hum. Mol. Genet. 2005, 14: 3337-3345.
11—Yu Feng, Agnes Vetro, Enito Kiss, Krisztina Kapornai, Gabriella Daroczi, Laszlo Mayer, Zsuzsana Tamas, Ildiko Baji. Julia Gadoros, Nicole King, James L. Kennedy, Karen Wigg, Maria Kovacs. Cathy L. Barr: Association of the Neurotrophic Tyrosine Kinase Receptor 3 (NTRK3) Gene and Childhood-Onset Mood Disorders. Am. J. Psychiatry 2008, 154: 610-616.
12—Ranjana Verma, Peter Holmans, James A. Knowles, Deepak Grover, Oleg V. Evgrafov, Raymond R. Crowe, William A. Scheftner, Myrna M. Weissman, J. Raymond DePaulo Jr., James B. Potash, and Douglas F. Levinson: Linkage Desiquilibrium Mapping of a Chromosome 15q25-26 Major Depression Linkage Region and Sequencing of NTRK3. Biol. Psychiatry 2008, 63: 1185-1189.
13—Peng Wang, Ping Wu, Robert W. Egan, M. Motasim Billah: Human phosphodiesterase 8A splice variants: cloning, gene organization, and tissue distribution. Gene 2001, 280: 183-194.

14—Charles L. raison, Andrey S. Borisov, Matthias Majer, Daniel F. Drake, Giuseppe Pagnoni, Bobbi J. Woolwine, Gerald J. Vogt, Breanne Massung, and Andrew H. Miller: Activation of Inflamatory Pathways by Interferon-alpha: Relationship to Monoamines and Depression. Biol. Psychiatry 2009, 65: 296-303.

15—Weidong Yang, Qindge Wang, Stephen J. Kanes, John M. Murray, Kazuko Nishikura: Altered RNA editing of serotonin 5-HT2c receptor induced by interferon: implications for depression associated with cytokine therapy. Mol. Brain Res. 2004, 124: 70-78.

16—Alain Poyau, Laurent Vincent, Hervé Berthommé, Catherine Paul, Brigitte Nicolas, Jean-Frangois Pujol, Jean-Jacques Madjar: Identification and relative quantification of adenosine to inosine editing in scrotonin 2c receptor mRNA by CE. Electrophoresis 2007, 28: 2843-2852.

The invention claimed is:

1. An in vitro method, comprising:
   a) providing a biological sample comprising mammalian cells derived from a cell line, wherein the mammalian cells are capable of expressing the editing enzymes ADARIa, ADARIb, and ADAR2 and the phosphodiesterase subtype 8A (PDE8A);
   b) preparing a cellular RNA extract from the biological sample; and
   c) determining the editing profile of the PDE8A pre-mRNA in said cellular RNA extract;
   wherein determining the editing profile of the PDE8A pre-mRNA comprises detecting the ned (non edited isoform) and B isoforms.

2. The method according to claim 1, wherein the cell line is an evolved primate tumor cell line.

3. The method according to claim 1, wherein the cell line is selected from the group consisting of a neuroblastoma cell line, a glioblastoma cell line, and an astrocytome cell line.

4. The method according to claim 1, wherein the cell line is SH-SY5Y.

5. The method according to claim 1, wherein the cell line is a recombinant cell line transformed by a vector carrying a nucleic acid encoding for at least one of an evolved primate ADARS isotype selected from ADARIa, ADARIb, and ADAR2, or an evolved primate PDE8A.

6. The method according to claim 1,
   further comprising measuring expression of the editing enzymes ADAR1a, ADAR1b, and ADAR2 in the biological sample.

7. The method according to claim 1,
   further comprising measuring expression of mRNAs encoding ADAR1a, ADAR1b, and ADAR2 in the cellular RNA extract.

8. The method according to claim 6, wherein expression of said editing enzymes ADAR1a, ADAR1b, and ADAR2 in the biological sample is measured quantitatively.

9. The method according to claim 1, wherein c) comprises detecting the ned, B, and AB isoforms.

10. The method according to claim 1, wherein c) comprises detecting the ned, B, AB, and BC isoforms.

11. The method according to claim 1 wherein a) comprises:
   contacting the mammalian cells with a test compound to obtain treated cells; and wherein the method further comprises:
   d) comparing the results obtained in c) between the treated cells obtained in a) and non-treated control cells; and
   e) evaluating an alteration of the editing profile of the PDE8A pre-mRNA obtained by the test compound in the treated cells which allows determining of potential toxicity or side-effects of the test compound.

12. The method according to claim 1, wherein a) further comprises contacting the mammalian cells with a test compound to obtain treated cells; and wherein the method further comprises:
- d) comparing the results obtained in c) between the treated cells obtained in a) and non-treated control cells; and
- e) evaluating an alteration of the editing profile of the PDE8A pre-mRNA obtained by contacting said test compound with the mammalian cells to obtain the treated cells, and selecting said compound for prevention or treatment of a pathology when the obtained alteration is a desired alteration.

13. The method of claim 12, wherein the pathology to be prevented or to be treated is selected from the group consisting of psychiatric disorders, mental disorders, schizophrenia, depression, Bipolar disease, suicide, abnormal feeding behaviour, Mild Cognitive Impairment (MCI), Epilepsia, Alzheimer, and Chronical pain syndromes.

14. The method according to claim 1, wherein the editing profile of the PDE8A pre-mRNA is determined by a process comprising performing a reverse transcription reaction on the cellular RNA extract and performing a nested type PCR comprising two rounds of PCR on the product of the reverse transcription, and wherein:
a) the first round of PCR is carried out by the following sets of primers:
Forward:
PDE8A-1FWD (SEQ ID NO. 13) GCTGAAGCCTTCCTTCTAAGG,
Reverse:
PDE8A-1REV (SEQ ID NO. 12) GGACCTAGAGTTGACCCAGG, and
and wherein
b) the second round of PCR is carried out by the following set of primers:
Forward:
PDE 8 A-2Fwd FAM (SEQ ID NO. 10) CTAGGGAACCCTGTTTAGTCC,
Reverse:
PDE8A-2Rev VIC (SEQ ID NO. 11) CAATGGGCACCAAAAAAGGG.

15. The method according to claim 1, wherein ADARs specific isoforms are determined in the method, and wherein the pair of primers specific for the human ADAR mRNA PCR amplification are selected from the group consisting of:
(A) for ADAR1-150 isoform mRNA amplification:
Forward: 5'-GCCTCGCGGGCGCAATGAATCC-3' (SEQ ID NO. 14),
Reverse: 5'-CTTGCCCTTCTTTGCCAGGGAG-3' (SEQ ID NO. 15);
(B) for ADAR1-110 isoform mRNA amplification:
Forward: 5'-CGAGCCATCATGGAGATGCCCTCC-3' (SEQ ID NO. 16),
Reverse: 5'-CATAGCTGCATCCTGCTTGGCCAC-3' (SEQ ID NO. 17); and
(C) for ADAR2 mRNA amplification:
Forward: 5'-GCTGCGCAGTCTGCCCTGGCCGC-3' (SEQ ID NO. 18),
Reverse: 5'-GTCATGACGACTCCAGCCAGCAC-3' (SEQ ID NO. 19).

* * * * *